US011938054B2

(12) United States Patent
Jones et al.

(10) Patent No.: US 11,938,054 B2
(45) Date of Patent: Mar. 26, 2024

(54) BODILY WASTE AND FLUID COLLECTION WITH SACRAL PAD

(71) Applicant: PureWick Corporation, El Cajon, CA (US)

(72) Inventors: Jill W. Jones, Avondale Estates, GA (US); Hoang D. Nguyen, Smyrna, GA (US); Cecille Canary, Atlanta, GA (US); Chris M. Fodouop, Atlanta, GA (US); Caroline Bunn, Atlanta, GA (US); Collen Shields Bland, Marietta, GA (US)

(73) Assignee: PureWick Corporation, Covington, GA (US)

( * ) Notice: Subject to any disclaimer, the term of this patent is extended or adjusted under 35 U.S.C. 154(b) by 0 days.

(21) Appl. No.: 17/654,156

(22) Filed: Mar. 9, 2022

(65) Prior Publication Data

US 2022/0287867 A1    Sep. 15, 2022

Related U.S. Application Data

(60) Provisional application No. 63/159,280, filed on Mar. 10, 2021.

(51) Int. Cl.
*A61F 5/451* (2006.01)
*A61F 5/44* (2006.01)
*A61M 1/00* (2006.01)

(52) U.S. Cl.
CPC ............ *A61F 5/451* (2013.01); *A61F 5/4405* (2013.01); *A61F 5/4408* (2013.01); *A61M 1/60* (2021.05);

(Continued)

(58) Field of Classification Search
CPC ...... A61F 5/451; A61F 5/4405; A61F 5/4408; A61F 5/443; A61F 5/4401; A61F 5/455;
(Continued)

(56) References Cited

U.S. PATENT DOCUMENTS 1,032,841 A    7/1912   Koenig
1,742,080 A    12/1929  Jones
(Continued)

FOREIGN PATENT DOCUMENTS

CA    3098571 A1    11/2019
CN    2269203 Y     12/1997
(Continued)

OTHER PUBLICATIONS

US 9,908,683 B2, 03/2018, Sandhausen et al. (withdrawn)
(Continued)

*Primary Examiner* — Ariana Zimbouski

(57) ABSTRACT

Examples relate to apparatuses, devices, systems, and methods for collecting bodily waste and bodily fluid using a sacral pad as an attachment point. The bodily waste collection apparatus includes a sacral pad and a bodily waste collection device attached to a lower portion of the sacral pad. The bodily waste collection device includes a fluid impermeable casing defining an interior region therein, a permeable material at least partially disposed in the interior region, and a conduit disposed within the bodily waste collection device. The sacral pad secures to the wearer and the bodily waste collection devices is at least partially maintained in a position to receive bodily waste from a wearer by the sacral pad.

25 Claims, 12 Drawing Sheets

(52) U.S. Cl.
CPC .............. *A61M 2202/0496* (2013.01); *A61M 2202/068* (2013.01)

(58) Field of Classification Search
CPC ............ A61M 1/60; A61M 2202/0496; A61M 2202/068; A61M 2210/1067
See application file for complete search history.

(56) References Cited

U.S. PATENT DOCUMENTS

| | | |
|---|---|---|
| 1,979,899 A | 11/1934 | Obrien et al. |
| 2,326,881 A | 8/1943 | Packer |
| 2,613,670 A | 10/1952 | Edward |
| 2,644,234 A | 7/1953 | Earl |
| 2,859,786 A | 11/1958 | Tupper |
| 2,968,046 A | 1/1961 | Duke |
| 2,971,512 A | 2/1961 | Reinhardt |
| 3,087,938 A | 4/1963 | Hans et al. |
| 3,198,994 A | 8/1965 | Hildebrandt et al. |
| 3,221,742 A | 12/1965 | Egon |
| 3,312,981 A | 4/1967 | McGuire et al. |
| 3,349,768 A | 10/1967 | Keane |
| 3,362,590 A | 1/1968 | Gene |
| 3,366,116 A | 1/1968 | Huck |
| 3,398,848 A | 8/1968 | Donovan |
| 3,400,717 A | 9/1968 | Bruce et al. |
| 3,406,688 A | 10/1968 | Bruce |
| 3,425,471 A | 2/1969 | Yates |
| 3,511,241 A | 5/1970 | Lee |
| 3,512,185 A | 5/1970 | Ellis |
| 3,520,300 A | 7/1970 | Flower |
| 3,528,423 A | 9/1970 | Lee |
| 3,613,123 A | 10/1971 | Langstrom |
| 3,651,810 A | 3/1972 | Ormerod |
| 3,699,815 A | 10/1972 | Holbrook |
| 3,726,277 A | 4/1973 | Hirschman |
| 3,843,016 A | 10/1974 | Bornhorst et al. |
| 3,863,798 A | 2/1975 | Kurihara et al. |
| 3,915,189 A | 10/1975 | Holbrook et al. |
| 3,998,228 A | 12/1976 | Poidomani |
| 3,999,550 A | 12/1976 | Martin |
| 4,015,604 A | 4/1977 | Csillag |
| 4,020,843 A | 5/1977 | Kanall |
| 4,022,213 A | 5/1977 | Stein |
| 4,027,776 A | 6/1977 | Douglas |
| 4,180,178 A | 12/1979 | Turner |
| 4,187,953 A | 2/1980 | Turner |
| 4,194,508 A | 3/1980 | Anderson |
| 4,200,102 A | 4/1980 | Duhamel et al. |
| 4,202,058 A | 5/1980 | Anderson |
| 4,233,025 A | 11/1980 | Larson et al. |
| 4,233,978 A | 11/1980 | Hickey |
| 4,246,901 A | 1/1981 | Frosch et al. |
| 4,257,418 A | 3/1981 | Hessner |
| 4,270,539 A | 6/1981 | Frosch et al. |
| 4,292,916 A | 10/1981 | Bradley et al. |
| 4,352,356 A | 10/1982 | Tong |
| 4,360,933 A | 11/1982 | Kimura et al. |
| 4,365,363 A | 12/1982 | Windauer |
| 4,387,726 A | 6/1983 | Denard |
| 4,425,130 A | 1/1984 | Desmarais |
| 4,446,986 A | 5/1984 | Bowen et al. |
| 4,453,938 A | 6/1984 | Brendling |
| 4,457,314 A | 7/1984 | Knowles |
| 4,476,879 A | 10/1984 | Jackson |
| 4,526,688 A | 7/1985 | Schmidt et al. |
| 4,528,703 A | 7/1985 | Kraus |
| D280,438 S | 9/1985 | Wendt |
| 4,553,968 A | 11/1985 | Komis |
| 4,581,026 A | 4/1986 | Schneider |
| 4,610,675 A | 9/1986 | Triunfol |
| 4,626,250 A | 12/1986 | Schneider |
| 4,627,846 A | 12/1986 | Ternstroem |
| 4,631,061 A | 12/1986 | Martin |
| 4,650,477 A | 3/1987 | Johnson |
| 4,656,675 A | 4/1987 | Fajnsztajn |
| 4,692,160 A | 9/1987 | Nussbaumer |
| 4,707,864 A | 11/1987 | Ikematsu et al. |
| 4,713,066 A | 12/1987 | Komis |
| 4,747,166 A | 5/1988 | Kuntz |
| 4,752,944 A | 6/1988 | Conrads et al. |
| 4,769,215 A | 9/1988 | Ehrenkranz |
| 4,772,280 A | 9/1988 | Rooyakkers |
| 4,790,830 A | 12/1988 | Hamacher |
| 4,790,835 A | 12/1988 | Elias |
| 4,791,686 A | 12/1988 | Taniguchi et al. |
| 4,795,449 A | 1/1989 | Schneider et al. |
| 4,799,928 A | 1/1989 | Crowley |
| 4,804,377 A | 2/1989 | Hanifl et al. |
| 4,812,053 A | 3/1989 | Bhattacharjee |
| 4,820,297 A | 4/1989 | Kaufman et al. |
| 4,846,818 A | 7/1989 | Keldahl et al. |
| 4,846,909 A | 7/1989 | Klug et al. |
| 4,882,794 A | 11/1989 | Stewart |
| 4,883,465 A | 11/1989 | Brennan |
| 4,886,508 A | 12/1989 | Washington |
| 4,886,509 A | 12/1989 | Mattsson |
| 4,889,533 A | 12/1989 | Beecher |
| 4,903,254 A | 2/1990 | Haas |
| 4,905,692 A | 3/1990 | More |
| 4,955,922 A | 9/1990 | Terauchi |
| 4,965,460 A | 10/1990 | Tanaka et al. |
| 4,987,849 A | 1/1991 | Sherman |
| 5,002,541 A | 3/1991 | Conkling et al. |
| 5,004,463 A | 4/1991 | Nigay |
| 5,031,248 A | 7/1991 | Kemper |
| 5,045,077 A | 9/1991 | Blake |
| 5,045,283 A | 9/1991 | Patel |
| 5,049,144 A | 9/1991 | Payton |
| 5,053,339 A | 10/1991 | Patel |
| 5,058,088 A | 10/1991 | Haas et al. |
| 5,071,347 A | 12/1991 | McGuire |
| 5,084,037 A | 1/1992 | Barnett |
| 5,100,396 A | 3/1992 | Zamierowski |
| 5,147,301 A | 9/1992 | Ruvio |
| 5,195,997 A | 3/1993 | Carns |
| 5,203,699 A | 4/1993 | McGuire |
| 5,244,458 A | 9/1993 | Takasu |
| 5,267,988 A | 12/1993 | Farkas |
| 5,275,307 A | 1/1994 | Freese |
| 5,294,983 A | 3/1994 | Ersoz et al. |
| 5,295,983 A | 3/1994 | Kubo |
| 5,300,052 A | 4/1994 | Kubo |
| 5,382,244 A | 1/1995 | Telang |
| 5,423,784 A | 6/1995 | Metz |
| 5,466,229 A | 11/1995 | Elson et al. |
| 5,478,334 A | 12/1995 | Bernstein |
| 5,499,977 A | 3/1996 | Marx |
| 5,543,042 A | 8/1996 | Filan et al. |
| D373,928 S | 9/1996 | Green |
| 5,618,277 A | 4/1997 | Goulter |
| 5,628,735 A | 5/1997 | Skow |
| 5,636,643 A | 6/1997 | Argenta et al. |
| 5,637,104 A | 6/1997 | Ball et al. |
| 5,674,212 A | 10/1997 | Osborn et al. |
| 5,678,564 A | 10/1997 | Lawrence et al. |
| 5,678,654 A | 10/1997 | Uzawa |
| 5,687,429 A | 11/1997 | Rahlff |
| 5,695,485 A | 12/1997 | Duperret et al. |
| 5,752,944 A | 5/1998 | Dann et al. |
| 5,772,644 A | 6/1998 | Bark et al. |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,865,378 A | 2/1999 | Hollinshead et al. |
| 5,865,819 A | 2/1999 | Cisko et al. |
| 5,887,291 A | 3/1999 | Bellizzi |
| 5,894,608 A | 4/1999 | Birbara |
| D409,303 S | 5/1999 | Oepping |
| 5,911,222 A | 6/1999 | Lawrence et al. |
| 5,957,904 A | 9/1999 | Holland |
| 5,958,213 A | 9/1999 | Goto |
| 5,972,505 A | 10/1999 | Phillips et al. |
| 6,059,762 A | 5/2000 | Boyer et al. |

(56) References Cited

U.S. PATENT DOCUMENTS

| | | |
|---|---|---|
| 6,063,064 A | 5/2000 | Tuckey et al. |
| 6,105,174 A | 8/2000 | Karlsten et al. |
| 6,113,582 A | 9/2000 | Dwork |
| 6,117,163 A | 9/2000 | Bierman |
| 6,123,398 A | 9/2000 | Arai et al. |
| 6,129,718 A | 10/2000 | Wada et al. |
| 6,131,964 A | 10/2000 | Sareshwala |
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,248,096 B1 | 6/2001 | Dwork et al. |
| 6,311,339 B1 | 11/2001 | Kraus |
| 6,336,919 B1 | 1/2002 | Davis et al. |
| 6,338,729 B1 | 1/2002 | Wada et al. |
| 6,409,712 B1 | 6/2002 | Dutari et al. |
| 6,416,500 B1 | 7/2002 | Wada et al. |
| 6,428,521 B1 | 8/2002 | Droll |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,540,729 B1 | 4/2003 | Wada et al. |
| 6,547,771 B2 | 4/2003 | Robertson et al. |
| 6,569,133 B2 | 5/2003 | Cheng et al. |
| D476,518 S | 7/2003 | Doppelt |
| 6,592,560 B2 | 7/2003 | Snyder et al. |
| 6,618,868 B2 | 9/2003 | Minnick |
| 6,620,142 B1 | 9/2003 | Flueckiger |
| 6,629,651 B1 | 10/2003 | Male et al. |
| 6,635,038 B2 | 10/2003 | Scovel |
| 6,652,495 B1 | 11/2003 | Walker |
| 6,685,684 B1 | 2/2004 | Falconer |
| 6,702,793 B1 | 3/2004 | Sweetser et al. |
| 6,706,027 B2 | 3/2004 | Harvie et al. |
| 6,732,384 B2 | 5/2004 | Scott |
| 6,736,977 B1 | 5/2004 | Hall et al. |
| 6,740,066 B2 | 5/2004 | Wolff et al. |
| 6,764,477 B1 | 7/2004 | Chen et al. |
| 6,783,519 B2 | 8/2004 | Samuelsson |
| 6,796,974 B2 | 9/2004 | Palumbo et al. |
| 6,814,547 B2 | 11/2004 | Childers et al. |
| 6,849,065 B2 | 2/2005 | Schmidt et al. |
| 6,857,137 B2 | 2/2005 | Otto |
| 6,885,690 B2 | 4/2005 | Aggerstam et al. |
| 6,888,044 B2 | 5/2005 | Fell et al. |
| 6,912,737 B2 | 7/2005 | Ernest et al. |
| 6,918,899 B2 | 7/2005 | Harvie |
| 6,979,324 B2 | 12/2005 | Bybordi et al. |
| 7,018,366 B2 | 3/2006 | Easter |
| 7,066,411 B2 | 6/2006 | Male et al. |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,171,699 B2 | 2/2007 | Ernest et al. |
| 7,171,871 B2 | 2/2007 | Kozak |
| 7,179,951 B2 | 2/2007 | Krishnaswamy-Mirle et al. |
| 7,181,781 B1 | 2/2007 | Trabold et al. |
| 7,186,245 B1 | 3/2007 | Cheng et al. |
| 7,192,424 B2 | 3/2007 | Cooper |
| 7,220,250 B2 | 5/2007 | Suzuki et al. |
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,488,310 B2 | 2/2009 | Yang |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,588,560 B1 | 9/2009 | Dunlop |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns et al. |
| D625,407 S | 10/2010 | Koizumi et al. |
| 7,806,879 B2 | 10/2010 | Brooks et al. |
| 7,815,067 B2 | 10/2010 | Matsumoto et al. |
| 7,833,169 B2 | 11/2010 | Hannon |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,353,074 B2 | 1/2013 | Krebs |
| 8,353,886 B2 | 1/2013 | Bester et al. |
| D676,241 S | 2/2013 | Merrill |
| 8,388,588 B2 | 3/2013 | Wada et al. |
| D679,807 S | 4/2013 | Burgess et al. |
| 8,425,482 B2 | 4/2013 | Khoubnazar |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,546,639 B2 | 10/2013 | Wada et al. |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,652,112 B2 | 2/2014 | Johannison et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,864,730 B2 | 10/2014 | Conway et al. |
| 8,881,923 B2 | 11/2014 | Higginson |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,173,602 B2 | 11/2015 | Gilbert |

(56) References Cited

U.S. PATENT DOCUMENTS

| | | |
|---|---|---|
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,382,047 B2 | 7/2016 | Schmidtner et al. |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| D789,522 S | 6/2017 | Burgess et al. |
| 9,687,849 B2 | 6/2017 | Bruno et al. |
| 9,694,949 B2 | 7/2017 | Hendricks et al. |
| 9,788,992 B2 | 10/2017 | Harvie |
| D804,907 S | 12/2017 | Sandoval |
| 9,868,564 B2 | 1/2018 | McGirr et al. |
| D814,239 S | 4/2018 | Arora |
| D817,484 S | 5/2018 | Lafond |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 | 3/2019 | Sanchez et al. |
| D848,612 S | 5/2019 | Mozzicato et al. |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Mllarreal |
| 10,407,222 B2 | 9/2019 | Allen |
| 10,478,356 B2 | 11/2019 | Griffin |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| D901,214 S | 11/2020 | Hu |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,678 B2 | 4/2021 | Newton et al. |
| 10,974,874 B2 | 4/2021 | Ragias et al. |
| D923,365 S | 6/2021 | Wang |
| 11,027,900 B2 | 6/2021 | Liu |
| 11,045,346 B2 | 6/2021 | Argent et al. |
| D928,946 S | 8/2021 | Sanchez et al. |
| 2001/0054426 A1 | 12/2001 | Knudson et al. |
| 2002/0019614 A1 | 2/2002 | Woon |
| 2002/0026161 A1 | 2/2002 | Grundke |
| 2002/0087131 A1 | 7/2002 | Wolff et al. |
| 2002/0189992 A1 | 12/2002 | Schmidt et al. |
| 2003/0004436 A1 | 1/2003 | Schmidt et al. |
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1 | 10/2003 | Harvie |
| 2003/0233079 A1 | 12/2003 | Parks et al. |
| 2004/0006321 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 | 7/2004 | Easter |
| 2004/0176731 A1 | 9/2004 | Cheng et al. |
| 2004/0191919 A1 | 9/2004 | Unger et al. |
| 2004/0207530 A1 | 10/2004 | Nielsen |
| 2004/0236292 A1 | 11/2004 | Tazoe et al. |
| 2004/0254547 A1 | 12/2004 | Okabe et al. |
| 2005/0010182 A1 | 1/2005 | Parks et al. |
| 2005/0033248 A1 | 2/2005 | Machida et al. |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0137557 A1 | 6/2005 | Swiecicki et al. |
| 2005/0177070 A1 | 8/2005 | Levinson et al. |
| 2005/0197639 A1 | 9/2005 | Mombrinie |
| 2005/0277904 A1 | 12/2005 | Chase et al. |
| 2005/0279359 A1 | 12/2005 | LeBlanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0111648 A1 | 5/2006 | Vermaak |
| 2006/0155214 A1 | 7/2006 | Wightman |
| 2006/0200102 A1 | 9/2006 | Cooper |
| 2006/0229576 A1 | 10/2006 | Conway et al. |
| 2006/0231648 A1 | 10/2006 | Male et al. |
| 2006/0235359 A1 | 10/2006 | Marland |
| 2007/0006368 A1 | 1/2007 | Key et al. |
| 2007/0038194 A1 | 2/2007 | Wada et al. |
| 2007/0117880 A1 | 5/2007 | Elson et al. |
| 2007/0135786 A1 | 6/2007 | Schmidt et al. |
| 2007/0149935 A1 | 6/2007 | Dirico |
| 2007/0191804 A1 | 8/2007 | Coley |
| 2007/0214553 A1 | 9/2007 | Carromba et al. |
| 2007/0266486 A1 | 11/2007 | Ramirez |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0091153 A1 | 4/2008 | Harvie |
| 2008/0091158 A1 | 4/2008 | Yang |
| 2008/0234642 A1 | 9/2008 | Patterson et al. |
| 2008/0281282 A1 | 11/2008 | Finger et al. |
| 2008/0287894 A1 | 11/2008 | Van Den Heuvel et al. |
| 2009/0025717 A1 | 1/2009 | Pinel |
| 2009/0056003 A1 | 3/2009 | Ivie et al. |
| 2009/0065412 A1 | 3/2009 | Mbarki et al. |
| 2009/0192482 A1 | 7/2009 | Dodge et al. |
| 2009/0234312 A1 | 9/2009 | Otoole et al. |
| 2009/0251510 A1 | 10/2009 | Noro et al. |
| 2009/0264840 A1 | 10/2009 | Virginio |
| 2009/0270822 A1 | 10/2009 | Medeiros |
| 2009/0281510 A1 | 11/2009 | Fisher |
| 2010/0004612 A1 | 1/2010 | Thevenin |
| 2010/0174250 A1* | 1/2010 | Hu et al. ............... A61M 1/916 |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060300 A1 | 3/2011 | Weig et al. |

(56) References Cited

U.S. PATENT DOCUMENTS

| | | |
|---|---|---|
| 2011/0077495 A1 | 3/2011 | Gilbert |
| 2011/0077606 A1 | 3/2011 | Wilcox et al. |
| 2011/0137273 A1 | 6/2011 | Muellejans et al. |
| 2011/0172620 A1 | 7/2011 | Khambatta |
| 2011/0172625 A1 | 7/2011 | Wada et al. |
| 2011/0202024 A1 | 8/2011 | Cozzens |
| 2011/0240648 A1 | 10/2011 | Tucker |
| 2012/0035577 A1 | 2/2012 | Tomes et al. |
| 2012/0103347 A1 | 5/2012 | Wheaton et al. |
| 2012/0165768 A1 | 6/2012 | Sekiyama et al. |
| 2012/0165786 A1 | 6/2012 | Chappa et al. |
| 2012/0210503 A1 | 8/2012 | Anzivino et al. |
| 2012/0233762 A1 | 9/2012 | Huang |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0330256 A1 | 12/2012 | Wilcox et al. |
| 2013/0006206 A1 | 1/2013 | Wada et al. |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0292537 A1 | 11/2013 | Dirico |
| 2014/0031774 A1 | 1/2014 | Bengtson |
| 2014/0157499 A1 | 6/2014 | Suzuki et al. |
| 2014/0182051 A1 | 7/2014 | Tanimoto et al. |
| 2014/0196189 A1 | 7/2014 | Lee et al. |
| 2014/0276501 A1 | 9/2014 | Cisko |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0320583 A1 | 11/2015 | Harvie |
| 2015/0329255 A1 | 11/2015 | Rzepecki |
| 2015/0359660 A1 | 12/2015 | Harvie |
| 2015/0366699 A1 | 12/2015 | Nelson |
| 2016/0029998 A1 | 2/2016 | Brister et al. |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0278662 A1 | 9/2016 | Brister et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0367726 A1 | 12/2016 | Gratzer |
| 2016/0374848 A1 | 12/2016 | Sanchez et al. |
| 2017/0007438 A1 | 1/2017 | Harvie |
| 2017/0143534 A1 | 5/2017 | Sanchez |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1 | 9/2017 | Sanchez et al. |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0042748 A1 | 12/2017 | Griffin |
| 2017/0348139 A1 | 12/2017 | Newton et al. |
| 2017/0354532 A1 | 12/2017 | Holt |
| 2017/0354906 A1 | 12/2017 | Wu |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0127187 A1 | 5/2018 | Sewell |
| 2018/0200101 A1 | 7/2018 | Su |
| 2018/0228642 A1 | 8/2018 | Davis et al. |
| 2019/0021899 A1 | 1/2019 | Vlet |
| 2019/0038451 A1 | 2/2019 | Harvie |
| 2019/0100362 A1 | 4/2019 | Meyers et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0247222 A1 | 8/2019 | Ecklund et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085610 A1 | 3/2020 | Cohn et al. |
| 2020/0229964 A1 | 7/2020 | Staali et al. |
| 2020/0231343 A1 | 7/2020 | Freedman et al. |
| 2020/0255189 A1 | 8/2020 | Liu |
| 2020/0331672 A1 | 10/2020 | Bertram et al. |
| 2020/0367677 A1 | 11/2020 | Silsby et al. |
| 2020/0369444 A1 | 11/2020 | Silsby et al. |
| 2020/0385179 A1 | 12/2020 | McCourt |
| 2020/0390592 A1 | 12/2020 | Merrill |
| 2021/0008771 A1 | 1/2021 | Huber et al. |
| 2021/0009323 A1 | 1/2021 | Markarian et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0121318 A1 | 4/2021 | Pinlac |
| 2021/0154055 A1 | 5/2021 | Villarreal |
| 2021/0188680 A1 | 6/2021 | Kumkrong et al. |
| 2021/0220162 A1 | 7/2021 | Jamison |
| 2021/0220163 A1 | 7/2021 | Mayrand |
| 2021/0229877 A1 | 7/2021 | Ragias et al. |
| 2021/0330485 A1 | 10/2021 | Sexton et al. |
| 2021/0393433 A1* | 12/2021 | Godinez et al. ........ A61F 5/455 |
| 2022/0062023 A1 | 3/2022 | Walthall et al. |
| 2022/0287867 A1 | 9/2022 | Jones et al. |
| 2022/0379001 A1 | 12/2022 | Sharma et al. |
| 2023/0293336 A1 | 9/2023 | Sexton et al. |

FOREIGN PATENT DOCUMENTS

| | | |
|---|---|---|
| CN | 1332620 A | 1/2002 |
| CN | 1533755 A | 10/2004 |
| CN | 1602825 A | 4/2005 |
| CN | 1720888 A | 1/2006 |
| CN | 101262836 A | 9/2008 |
| CN | 202184840 U | 4/2012 |
| CN | 103717180 A | 4/2014 |
| CN | 106236363 A | 12/2016 |
| CN | 205849719 U | 1/2017 |
| CN | 107847384 A | 3/2018 |
| CN | 108354703 A | 8/2018 |
| CN | 108852605 A | 11/2018 |
| DE | 79818 C | 10/1893 |
| DE | 1516466 A1 | 6/1969 |
| DE | 9407554.9 U1 | 5/1995 |
| DE | 4443710 A1 | 6/1995 |
| DE | 19619597 A1 | 11/1997 |
| DE | 102011103783 A1 | 12/2012 |
| DK | 9600118 | 11/1996 |
| EP | 0032138 A2 | 7/1981 |
| EP | 0066070 B1 | 12/1982 |
| EP | 0119143 B1 | 11/1988 |
| EP | 0610638 A1 | 8/1994 |
| EP | 0613355 A1 | 9/1994 |
| EP | 0613355 B1 | 1/1997 |
| EP | 1332738 A1 | 8/2003 |

(56) References Cited

FOREIGN PATENT DOCUMENTS

| | | |
|---|---|---|
| EP | 1382318 A1 | 1/2004 |
| EP | 1382318 B1 | 5/2006 |
| EP | 2180907 A1 | 5/2010 |
| EP | 2380532 A1 | 10/2011 |
| EP | 2879534 B1 | 3/2017 |
| EP | 3424471 A1 | 1/2019 |
| EP | 3169292 B1 | 11/2019 |
| GB | 1011517 A | 12/1965 |
| GB | 1467144 A | 3/1977 |
| GB | 2106395 A | 4/1983 |
| GB | 2171315 A | 8/1986 |
| GB | 2148126 B | 7/1987 |
| GB | 2191095 A | 12/1987 |
| GB | 2199750 A | 7/1988 |
| GB | 2260907 A | 5/1993 |
| GB | 2462267 A | 2/2010 |
| GB | 2469496 A | 10/2010 |
| JP | S5410596 A | 1/1979 |
| JP | S5410596 Y2 | 5/1979 |
| JP | S5888596 U | 6/1983 |
| JP | S63107780 U | 7/1988 |
| JP | H0267530 A | 3/1990 |
| JP | H02103871 A | 4/1990 |
| JP | H0460220 A | 2/1992 |
| JP | H05123349 A | 5/1993 |
| JP | 3087938 B2 | 10/1995 |
| JP | H1040141 A | 2/1998 |
| JP | H11113946 A | 4/1999 |
| JP | H11290365 A | 10/1999 |
| JP | 2000185068 A | 7/2000 |
| JP | 2001054531 A | 2/2001 |
| JP | 2001276107 A | 10/2001 |
| JP | 2001276108 A | 10/2001 |
| JP | 2004130056 A | 4/2004 |
| JP | 2004267530 A | 9/2004 |
| JP | 2005066011 A | 3/2005 |
| JP | 2005066325 A | 3/2005 |
| JP | 2006026108 A | 2/2006 |
| JP | 3123547 B2 | 6/2006 |
| JP | 2006204868 A | 8/2006 |
| JP | 3132659 B2 | 5/2007 |
| JP | 4039641 B2 | 11/2007 |
| JP | 2010081981 A | 4/2010 |
| JP | 2010536439 A | 12/2010 |
| JP | 4747166 B2 | 5/2011 |
| JP | 2011224070 A | 11/2011 |
| JP | 2012523869 A | 10/2012 |
| JP | 2015092945 A | 5/2015 |
| JP | 3198994 B2 | 7/2015 |
| KR | 101432639 B1 | 8/2014 |
| KR | 102011420 B1 * | 7/2018 ........... A61F 5/4401 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9309736 A2 | 5/1993 |
| WO | 9309736 A3 | 6/1993 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0033773 A1 | 6/2000 |
| WO | 0057784 A1 | 10/2000 |
| WO | 0145618 A1 | 6/2001 |
| WO | 0145621 A1 | 6/2001 |
| WO | 0239937 A1 | 5/2002 |
| WO | 02094160 A1 | 11/2002 |
| WO | 03013967 A1 | 2/2003 |
| WO | 03024824 A1 | 3/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2005074571 A3 | 9/2005 |
| WO | 2005089687 A2 | 9/2005 |
| WO | 2005107661 A2 | 11/2005 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007134608 A2 | 11/2007 |
| WO | 2007128156 A3 | 2/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016124203 A1 | 8/2016 |
| WO | 2016139448 A1 | 9/2016 |
| WO | 2016166562 A1 | 10/2016 |
| WO | 2016167535 A1 | 10/2016 |
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017001846 A1 | 1/2017 |
| WO | 2017152198 A1 | 9/2017 |
| WO | 2017162559 A1 | 9/2017 |
| WO | 2017205446 A1 | 11/2017 |
| WO | 2017209779 A1 | 12/2017 |
| WO | 2017210524 A1 | 12/2017 |
| WO | 2018022414 A1 | 2/2018 |
| WO | 2018044781 A1 | 3/2018 |
| WO | 2018056953 A1 | 3/2018 |
| WO | 2018090550 A1 | 5/2018 |
| WO | 2018138513 A1 | 8/2018 |
| WO | 2018144463 A1 | 8/2018 |

(56) References Cited

FOREIGN PATENT DOCUMENTS

| | | |
|---|---|---|
| WO | 2018152156 A1 | 8/2018 |
| WO | 2018183791 A1 | 10/2018 |
| WO | 2018235026 A1 | 12/2018 |
| WO | 2018235065 A1 | 12/2018 |
| WO | 2019096845 A1 | 5/2019 |
| WO | 2019190593 A1 | 10/2019 |
| WO | 2019212949 A1 | 11/2019 |
| WO | 2019212950 A1 | 11/2019 |
| WO | 2019212951 A1 | 11/2019 |
| WO | 2019212952 A1 | 11/2019 |
| WO | 2019212954 A1 | 11/2019 |
| WO | 2019212955 A1 | 11/2019 |
| WO | 2019212956 A1 | 11/2019 |
| WO | 2019214788 A1 | 11/2019 |
| WO | 2019239433 A1 | 12/2019 |
| WO | 2020000994 A1 | 1/2020 |
| WO | 2020020618 A1 | 1/2020 |
| WO | 2020038822 A1 | 2/2020 |
| WO | 2020088409 A1 | 5/2020 |
| WO | 2020049394 A3 | 6/2020 |
| WO | 2020120657 A1 | 6/2020 |
| WO | 2020152575 A1 | 7/2020 |
| WO | 2020182923 A1 | 9/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016300 A1 | 1/2021 |
| WO | 2021034886 A1 | 2/2021 |
| WO | 2021041123 A1 | 3/2021 |
| WO | 2021094352 A1 | 5/2021 |
| WO | 2021155206 A1 | 8/2021 |
| WO | 2021207621 A1 | 10/2021 |
| WO | 2021257202 A1 | 12/2021 |
| WO | 2022006256 A1 | 1/2022 |

OTHER PUBLICATIONS

Advisory Action for U.S. Application No. 16/478,180 dated Sep. 21, 2022.
Advisory Action for U.S. Appl. No. 16/904,868 dated Jun. 15, 2022.
Final Office Action for U.S. Appl. No. 16/449,039 dated Aug. 1, 2022.
Final Office Action for U.S. Application No. 16/478,180 dated Jun. 22, 2022.
Final Office Action for U.S. Appl. No. 16/904,868 dated Mar. 10, 2022.
International Search Report and Written Opinion from International Application No. PCT/US2022/015471 dated May 16, 2022.
International Search Report and Written Opinion from International Application No. PCT/US2022/018170 dated May 31, 2022.
Issue Notification for U.S. Appl. No. 17/088,272 dated Jun. 15, 2022.
Issue Notification for U.S. Appl. No. 17/330,657 dated Jun. 22, 2022.
Non-Final Office Action for U.S. Appl. No. 16/433,773 dated Apr. 21, 2022.
Non-Final Office Action for U.S. Appl. No. 16/905,400 dated Apr. 27, 2022.
Notice of Allowance for U.S. Appl. No. 16/905,400 dated Aug. 17, 2022.
Notice of Allowance for U.S. Appl. No. 17/330,657 dated Mar. 16, 2022.
Notice of Allowance for U.S. Appl. No. 29/741,751 dated Jun. 9, 2022.
Advisory Action for U.S. Appl. No. 14/722,613 dated Mar. 4, 2019.
Advisory Action for U.S. Appl. No. 14/952,591 dated Jun. 1, 2018.
Advisory Action for U.S. Appl. No. 15/238,427 dated Apr. 10, 2019.
Advisory Action for U.S. Appl. No. 16/899,956 dated Jul. 9, 2021.
Advisory Action for U.S. Appl. No. 16/904,868 dated Jul. 2, 2021.
Advisory Action for U.S. Appl. No. 16/905,400 dated Feb. 16, 2022.
Advisory Action for U.S. Appl. No. 16/905,400 dated Jun. 9, 2021.
Corrected International Search Report and Written Opinion for International Application No. PCT/US2017/043025 dated Jan. 11, 2018.
Corrected Notice of Allowability for U.S. Application No. 15/221,106 dated Jul. 2, 2019.
Corrected Notice of Allowability for U.S. Appl. No. 15/612,325 dated Mar. 17, 2021.
Corrected Notice of Allowability for U.S. Appl. No. 17/330,657 dated Dec. 9, 2021.
Final Office Action for U.S. Appl. No. 14/722,613 dated Nov. 29, 2018.
Final Office Action for U.S. Appl. No. 14/947,759 dated Apr. 8, 2016.
Final Office Action for U.S. Appl. No. 14/952,591 dated Feb. 23, 2018.
Final Office Action for U.S. Appl. No. 14/952,591 dated Nov. 1, 2019.
Final Office Action for U.S. Appl. No. 14/952,591 dated Nov. 27, 2020.
Final Office Action for U.S. Appl. No. 15/171,968 dated Feb. 14, 2020.
Final Office Action for U.S. Appl. No. 15/171,968 dated Mar. 19, 2019.
Final Office Action for U.S. Appl. No. 15/221,106 dated Jan. 23, 2019.
Final Office Action for U.S. Appl. No. 15/238,427 dated Jan. 2, 2019.
Final Office Action for U.S. Appl. No. 15/260,103 dated Feb. 14, 2019.
Final Office Action for U.S. Appl. No. 15/612,325 dated Sep. 17, 2020.
Final Office Action for U.S. Appl. No. 16/899,956 dated Apr. 19, 2021.
Final Office Action for U.S. Appl. No. 16/904,868 dated Mar. 26, 2021.
Final Office Action for U.S. Appl. No. 16/905,400 dated Apr. 6, 2021.
Final Office Action for U.S. Appl. No. 16/905,400 dated Dec. 9, 2021.
Final Office Action for U.S. Appl. No. 17/088,272 dated May 25, 2021.
Final Office Action for U.S. Appl. No. 29/624,661 dated Feb. 18, 2020.
International Search Report and Written Opinion from International Application No. PCT/US2016/049274 dated Dec. 1, 2016.
International Search Report and Written Opinion from International Application No. PCT/US2017/035625 dated Aug. 15, 2017.
International Search Report and Written Opinion from International Application No. PCT/US2017/043025 dated Oct. 18, 2017.
International Search Report and Written Opinion from International Application No. PCT/US2018/015968 dated Apr. 6, 2018.
International Search Report and Written Opinion from International Application No. PCT/US2019/029608 dated Sep. 3, 2019.
International Search Report and Written Opinion from International Application No. PCT/US2019/029609 dated Sep. 3, 2019.
International Search Report and Written Opinion from International Application No. PCT/US2019/029610 dated Sep. 3, 2019.
International Search Report and Written Opinion from International Application No. PCT/US2019/029611 dated Jul. 3, 2019.
International Search Report and Written Opinion from International Application No. PCT/US2019/029613 dated Jul. 3, 2019.
International Search Report and Written Opinion from International Application No. PCT/US2019/029614 dated Sep. 26, 2019.
International Search Report and Written Opinion from International Application No. PCT/US2019/029616 dated Aug. 30, 2019.
International Search Report and Written Opinion from International Application No. PCT/US2020/023572 dated Jul. 6, 2020.
International Search Report and Written Opinion from International Application No. PCT/US2020/033064 dated Aug. 31, 2020.
International Search Report and Written Opinion from International Application No. PCT/US2020/033122 dated Aug. 31, 2020.

(56) References Cited

OTHER PUBLICATIONS

International Search Report and Written Opinion from International Application No. PCT/US2020/040860 dated Oct. 2, 2020.
International Search Report and Written Opinion from International Application No. PCT/US2020/041242 dated Nov. 17, 2020.
International Search Report and Written Opinion from International Application No. PCT/US2020/041249 dated Oct. 2, 2020.
International Search Report and Written Opinion from International Application No. PCT/US2020/042262 dated Oct. 14, 2020.
International Search Report and Written Opinion from International Application No. PCT/US2020/043059 dated Oct. 6, 2020.
International Search Report and Written Opinion from International Application No. PCT/US2020/044024 dated Nov. 12, 2020.
International Search Report and Written Opinion from International Application No. PCT/US2020/046914 dated Dec. 1, 2020.
International Search Report and Written Opinion from International Application No. PCT/US2020/055680 dated Dec. 15, 2020.
International Search Report and Written Opinion from International Application No. PCT/US2020/061563 dated Feb. 19, 2021.
International Search Report and Written Opinion from International Application No. PCT/US2020/065234 dated Apr. 12, 2021.
International Search Report and Written Opinion from International Application No. PCT/US2020/067451 dated Mar. 25, 2021.
International Search Report and Written Opinion from International Application No. PCT/US2020/067454 dated Mar. 29, 2021.
International Search Report and Written Opinion from International Application No. PCT/US2020/067455 dated Mar. 26, 2021.
International Search Report and Written Opinion from International Application No. PCT/US2021/015024 dated May 18, 2021.
International Search Report and Written Opinion from International Application No. PCT/US2021/015787 dated May 27, 2021.
International Search Report and Written Opinion from International Application No. PCT/US2021/023001 dated Jun. 21, 2021.
International Search Report and Written Opinion from International Application No. PCT/US2021/024162 dated Jul. 8, 2021.
International Search Report and Written Opinion from International Application No. PCT/US2021/027061 dated Jul. 19, 2021.
International Search Report and Written Opinion from International Application No. PCT/US2021/027104 dated Jul. 6, 2021.
International Search Report and Written Opinion from International Application No. PCT/US2021/027314 dated Jul. 6, 2021.
International Search Report and Written Opinion from International Application No. PCT/US2021/027422 dated Aug. 12, 2021.
International Search Report and Written Opinion from International Application No. PCT/US2021/027425 dated Aug. 11, 2021.
International Search Report and Written Opinion from International Application No. PCT/US2021/027913 dated Jul. 12, 2021.
International Search Report and Written Opinion from International Application No. PCT/US2021/027917 dated Aug. 19, 2021.
International Search Report and Written Opinion from International Application No. PCT/US2021/035181 dated Sep. 16, 2021.
International Search Report and Written Opinion from International Application No. PCT/US2021/043893 dated Nov. 22, 2021.
International Search Report and Written Opinion from International Application No. PCT/US2021/044699 dated Nov. 22, 2021.
International Search Report and Written Opinion from International Application No. PCT/US2021/045188 dated Jan. 26, 2022.
International Search Report and Written Opinion from International Application No. PCT/US2021/047536 dated Dec. 23, 2021.
International Search Report and Written Opinion from International Application No. PCT/US2021/048211 dated Dec. 22, 2021.
Issue Notification for U.S. Appl. No. 14/952,591 dated Jul. 28, 2021.
Issue Notification for U.S. Appl. No. 15/171,968 dated Mar. 3, 2021.
Issue Notification for U.S. Appl. No. 15/221,106 dated Jul. 24, 2019.
Issue Notification for U.S. Appl. No. 15/238,427 dated Jul. 24, 2019.
Issue Notification for U.S. Appl. No. 15/260,103 dated Aug. 7, 2019.
Issue Notification for U.S. Appl. No. 15/611,587 dated Feb. 20, 2019.
Issue Notification for U.S. Appl. No. 15/612,325 dated Mar. 24, 2021.
Issue Notification for U.S. Appl. No. 29/624,661 dated Aug. 4, 2021.
Non-Final Office Action for U.S. Appl. No. 14/592,591 dated Mar. 20, 2020.
Non-Final Office Action for U.S. Appl. No. 14/722,613 dated Jun. 13, 2019.
Non-Final Office Action for U.S. Appl. No. 14/947,759 dated Mar. 17, 2016.
Non-Final Office Action for U.S. Appl. No. 14/952,591 dated Aug. 1, 2017.
Non-Final Office Action for U.S. Appl. No. 14/952,591 dated Mar. 20, 2020.
Non-Final Office Action for U.S. Appl. No. 14/952,591 dated Mar. 21, 2019.
Non-Final Office Action for U.S. Appl. No. 14/952,591 dated Sep. 28, 2018.
Non-Final Office Action for U.S. Appl. No. 15/171,968 dated May 11, 2020.
Non-Final Office Action for U.S. Appl. No. 15/171,968 dated Aug. 20, 2019.
Non-Final Office Action for U.S. Appl. No. 15/171,968 dated Jun. 12, 2018.
Non-Final Office Action for U.S. Appl. No. 15/221,106 dated Jun. 5, 2018.
Non-Final Office Action for U.S. Appl. No. 15/238,427 dated Aug. 8, 2018.
Non-Final Office Action for U.S. Appl. No. 15/260,103 dated Sep. 26, 2018.
Non-Final Office Action for U.S. Appl. No. 15/611,587 dated Dec. 29, 2017.
Non-Final Office Action for U.S. Appl. No. 15/611,587 dated Jul. 13, 2018.
Non-Final Office Action for U.S. Appl. No. 15/612,325 dated Mar. 19, 2020.
Non-Final Office Action for U.S. Appl. No. 16/245,726 dated Jan. 21, 2022.
Non-Final Office Action for U.S. Appl. No. 16/449,039 dated Dec. 8, 2021.
Non-Final Office Action for U.S. Appl. No. 16/452,145 dated Sep. 28, 2021.
Non-Final Office Action for U.S. Appl. No. 16/452,258 dated Sep. 28, 2021.
Non-Final Office Action for U.S. Appl. No. 16/478,180 dated Oct. 22, 2021.
Non-Final Office Action for U.S. Appl. No. 16/899,956 dated Oct. 16, 2020.
Non-Final Office Action for U.S. Appl. No. 16/899,956 dated Sep. 2, 2021.
Non-Final Office Action for U.S. Appl. No. 16/904,868 dated Nov. 25, 2020.
Non-Final Office Action for U.S. Appl. No. 16/904,868 dated Oct. 5, 2021.
Non-Final Office Action for U.S. Appl. No. 16/905,400 dated Dec. 2, 2020.
Non-Final Office Action for U.S. Appl. No. 16/905,400 dated Jul. 22, 2021.
Non-Final Office Action for U.S. Appl. No. 17/088,272 dated Jan. 25, 2021.
Non-Final Office Action for U.S. Appl. No. 17/330,657 dated Aug. 11, 2021.
Non-Final Office Action for U.S. Appl. No. 29/624,661 dated Jul. 18, 2019.
Non-Final Office Action for U.S. Appl. No. 29/694,002 dated Jun. 24, 2020.
Non-Final Office Action for U.S. Appl. No. 29/741,751 dated Jan. 18, 2022.
Notice of Allowance for U.S. Appl. No. 14/952,591 dated Apr. 5, 2021.

(56) References Cited

OTHER PUBLICATIONS

Notice of Allowance for U.S. Appl. No. 14/952,591 dated Jul. 8, 2021.
Notice of Allowance for U.S. Appl. No. 15/171,968 dated Feb. 16, 2021.
Notice of Allowance for U.S. Appl. No. 15/171,968 dated Nov. 6, 2020.
Notice of Allowance for U.S. Appl. No. 15/221,106 dated May 1, 2019.
Notice of Allowance for U.S. Appl. No. 15/238,427 dated May 23, 2019.
Notice of Allowance for U.S. Appl. No. 15/260,103 dated Jun. 7, 2019.
Notice of Allowance for U.S. Appl. No. 15/611,587 dated Dec. 21, 2018.
Notice of Allowance for U.S. Appl. No. 15/612,325 dated Feb. 19, 2021.
Notice of Allowance for U.S. Appl. No. 15/612,325 dated Jan. 21, 2021.
Notice of Allowance for U.S. Appl. No. 16/899,956 dated Dec. 29, 2021.
Notice of Allowance for U.S. Appl. No. 17/088,272 dated Aug. 5, 2021.
Notice of Allowance for U.S. Appl. No. 17/088,272 dated Mar. 4, 2022.
Notice of Allowance for U.S. Appl. No. 17/088,272 dated Nov. 24, 2021.
Notice of Allowance for U.S. Appl. No. 17/330,657 dated Nov. 26, 2021.
Notice of Allowance for U.S. Appl. No. 29/624,661 dated Apr. 28, 2021.
Notice of Allowance for U.S. Appl. No. 29/624,661 dated Jul. 10, 2020.
Notice of Allowance for U.S. Appl. No. 29/624,661 dated May 14, 2020.
Notice of Allowance for U.S. Appl. No. 29/624,661 dated Sep. 29, 2020.
Notice of Allowance for U.S. Appl. No. 29/694,002 dated Apr. 29, 2021.
Notice of Allowance for U.S. Appl. No. 29/694,002 dated Jan. 29, 2021.
Notice of Allowance for U.S. Appl. No. 29/694,002 dated Oct. 16, 2020.
Notice to File Missing Parts for U.S. Appl. No. 17/179,116 dated Mar. 3, 2021.
Restriction Requirement for U.S. Appl. No. 16/433,773 dated Dec. 7, 2021.
Restriction Requirement for U.S. Appl. No. 16/478,180 dated May 25, 2021.
U.S. Appl. No. 17/653,314, filed Mar. 3, 2022.
U.S. Appl. No. 14/433,773, filed Apr. 3, 2020.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/384,196, filed Dec. 19, 2016.
U.S. Appl. No. 15/611,587, filed Jun. 1, 2017.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036, filed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,920, filed Mar. 8, 2022.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,977, filed Jan. 30, 2020.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.

(56) References Cited

OTHER PUBLICATIONS

U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
Sage's Second Supplemental Invalidity Contentions Regarding U.S. Pat. No. 8,287,508, U.S. Pat. No. 10,226,375, U.S. Pat. No. 10,390,989, and U.S. Pat. No. 10,376,407, 292 pages.
Plaintiff's Identification of Claim Terms and Proposed Constructions, 3 pages.
Sage's Preliminary Identification of Claim Elements and Proposed Constructions for U.S. Pat. No. 8,287,508, U.S. Pat. No. 10,226,376, U.S. Pat. No. 10,390,989 and U.S. Pat. No. 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. No. 8,287,508; U.S. Pat. No. 10,226,375; U.S. Pat. No. 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. No. 8,287,508; U.S. Pat. No. 10,226,375; and U.S. Pat. No. 10,390,989, May 29, 2020, 193 pages.
Defendant and Counterclaim Plaintiff Sage Products, LLC's Answer, Defenses, and Counterclaims to Plaintiff's Amended Complaint, Nov. 1, 2019.
Plaintiff's Opening Claim Construction Brief, Oct. 16, 2020, 26 pages.
"3 Devices Take Top Honors in Dare-to-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover-Catheter Bag Cover 2000 ml Volume-Medline Style-Multiple Sclerosis-Spine Injury-Suprapubic Catheter-

(56) References Cited

OTHER PUBLICATIONS

Bladder Incontinence", https://www.etsy.com/listing/1142934658/urine-bag-cover-caatheter-bag-cover-2000, 2022, 1 page.

"User & Maintenance Guide", Omni Medical, 2007, 16 pages.

"Vinyl Dust Cover, Janome #741811000, Janome, Sewing Parts Online", https://www.sewingpartsonline.com/vinyl-dust-cover-janome-74181000, 2020, 2 pages.

"Winners Announced for Dare-to-Dream Medtech Design Challenge", https://www.mddionline.com/design-engineering/winners-announced-dare-dream-medtech-design-challenge, 2014, 4 pages.

Ali, "Sustainability Assessment: Seventh Generation Diapers versus gDiapers", The University of Vermont, Dec. 6, 2011, pp. 1-31.

Autumn, et al., "Frictional adhesion: a new angle on gecko attachment", The Journal of Experimental Biology, 2006, pp. 3569-3579.

Cañas, et al., "Effect of nano- and micro-roughness on adhesion of bioinspired micropatterned surfaces", Acta Biomaterialia 8, 2012, pp. 282-288.

Chaudhary, et al., "Bioinspired dry adhesive: Poly(dimethylsiloxane) grafted with poly(2-ethylhexyl acrylate) brushes", European Polymer Journal, 2015, pp. 432-440.

Dai, et al., "Non-sticky and Non-slippery Biomimetic Patterned Surfaces", Journal of Bionic Engineering, Mar. 2020, pp. 326-334.

Espinoza-Ramirez, "Nanobiodiversity and Biomimetic Adhesives Development: From Nature to Production and Application", Journal of Biomaterials and Nanobiotechnology, pp. 78-101, 2019.

Hollister, "Female Urinary and Pouch and Male Urinary Pouch Brochure", 2011, 1 page.

Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device.

Hollister, "Retracted Penis Pouch by Hollister", Vitality Medical. com, 6 pages.

Hwang, et al., "Multifunctional Smart Skin Adhesive Patches for Advanced Health Care", Adv. Healthcare Mater, 2018, pp. 1-20.

Jagota, et al., "Adhesion, friction, and compliance of bio-mimetic and bio-inspired structured interfaces", Materials Science and Engineering, 2011, pp. 253-292.

Jeong, et al., "A nontransferring dry adhesive with hierarchical polymer nanohairs", PNAS, Apr. 7, 2009, pp. 5639-5644.

Jeong, et al., "Nanohairs and nanotubes: Efficient structural elements for gecko-inspired artificial dry adhesives", Science Direct, 2009, pp. 335-346.

Karp, et al., "Dry solution to a sticky problem", Nature., 2011, pp. 42-43.

Lee, et al., "Continuous Fabrication of Wide-Tip Microstructures for Bio-Inspired Dry Adhesives via Tip Inking Process", Journal of Chemistry, Jan. 2, 2019, pp. 1-5.

Macaulay, et al., "A Noninvasive Continence Management System: Development and Evaluation of a Novel Toileting Device for Women", The Wound, Ostomy and Continence Nurses Society, 2007, pp. 641-648.

Newman, et al., "The Urinary Incontinence Sourcebook", Petition for Interparties Review, 1997, 23 pages.

Newton, et al., "Measuring Safety, Effectiveness and Ease of Use of PureWick in the Management of Urinary Incontinence in Bedbound Women: Case Studies", Jan. 8, 2016, 11 pages.

Parmar, "10 Finalists Chosen for Dare-to-Dream Medtech Design Challenge (PureWick)", Design Services, Nov. 10, 2014, 3 pages.

Parness, et al., "A microfabricated wedge-shaped adhesive array displaying gecko-like dynamic adhesion, directionality", J.R. Soc. Interface, 2009, pp. 1223-1232.

Purewick, "Incontinence Relief for Women", Presentation, Sep. 23, 2015, 7 pages.

Pytlik, "Super Absorbent Polymers", University of Buffalo.

Sachtman, "New Relief for Pilots? It Depends", Wired, 2008, 2 pages.

Tsipenyuk, et al., "Use of biomimetic hexagonal surface texture in friction against lubricated skin", Journal of the Royal Society—Interface, 2014, pp. 1-6.

Non-Final Office Action for U.S. Appl. No. 17/494,578 dated Mar. 2, 2023.

Restriction Requirement for U.S. Appl. No. 17/412,864 dated Apr. 19, 2023.

U.S. Appl. No. 17/999,648, filed Nov. 22, 2022.

Non-Final Office Action for U.S. Appl. No. 17/412,864 dated Sep. 28, 2023.

Issue Notification for U.S. Appl. No. 17/494,578 dated Nov. 22, 2023.

\* cited by examiner

BODILY WASTE AND FLUID COLLECTION WITH SACRAL PAD

CROSS-REFERENCE TO RELATED APPLICATIONS

This application claims priority to U.S. Provisional Patent Application No. 63/159,280 filed on 10 Mar. 2021, the disclosure of which is incorporated herein, in its entirety, by this reference.

BACKGROUND

An individual may have limited or impaired mobility such that bowel movements and urination in a restroom are challenging or impossible. For example, the individual may have a condition, had a surgery, or a have disability that impairs mobility. Additionally, fluid or stool collection from the individual may be needed for monitoring purposes, hygiene, prevention of injuries, or clinical testing.

Clothing, beds, and bedding for treating such individuals may become soiled during use. Such clothing, beds, and bedding may be may be prone to discomfort and unintentional soiling if conventional urine and fecal collection devices, such as bedpans or the like are used. Thus, users and providers of bodily waste and fluid collection devices continue to seek new and improved apparatuses, devices, systems, and methods to collect bodily waste and fluids.

SUMMARY

Embodiments disclosed herein are related to devices, systems, and methods for collecting bodily waste and bodily fluid using a sacral pad as an attachment point. In an embodiment, a bodily waste collection apparatus is disclosed. The bodily waste collection apparatus includes a sacral pad. The bodily waste collection apparatus includes a bodily waste collection device attached to a lower portion of the sacral pad. The bodily waste collection device includes a fluid impermeable casing defining an interior region therein, a permeable material at least partially disposed in the interior region, and a conduit disposed within the bodily waste collection device.

In an embodiment, a bodily waste collection system is disclosed. The bodily waste collection system includes at least one fluid storage container configured to hold a fluid. The bodily waste collection system includes a bodily waste collection apparatus having a sacral pad and a bodily waste collection device. The bodily waste collection device includes a fluid impermeable casing defining an interior region therein, a permeable material at least partially disposed in the interior region, and a conduit disposed within the bodily waste collection device. The bodily waste collection system includes at least one vacuum source fluidly connected to the at least one of the fluid storage container via the conduit, the at least one vacuum source configured to draw fluid into the at least one fluid storage container from the bodily waste collection device via the conduit.

In an embodiment, a method for collecting bodily waste is disclosed. The method includes positioning a bodily waste collection apparatus on a wearer, the bodily waste collection apparatus including a sacral pad a bodily waste collection device attached to a lower portion of the sacral pad. The bodily waste collection device includes a fluid impermeable casing defining an interior region therein, a permeable material at least partially disposed in the interior region, and a conduit disposed within the bodily waste collection device. The method includes receiving liquid waste in the bodily waste collection device. The method includes removing at least some of the liquid waste from the bodily waste collection device via the conduit.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Embodiments disclosed herein are related to devices, systems, and methods for collecting bodily waste and bodily fluid using a sacral pad as an attachment point. The devices, systems, and methods of disclosed herein include a bodily waste collection apparatus for attaching to the sacrum of a wearer and collecting at least a portion of bodily waste passed through the anus of the wearer, such as semi-liquid or liquid stool, as well as urine or vaginal discharge. The bodily waste collection apparatus can include a fluid collection device for collecting fluid discharged through the urethra of the wearer.

The apparatuses, devices, systems, and methods herein allow care providers to prevent bedsores on the wearer's sacrum, maintain position of the bodily waste collection apparatus with respect to the wearer's anus, and limit or prevent bodily waste and liquids from contacting the skin of the wearer. Such bodily waste and liquid control allow care providers to keep the wearer's skin dry which prevents bedsores, infections, soiled clothing, and soiled bedding. The apparatuses, devices, systems, and methods herein also limit the necessity for care providers to clean the wearer due to bowel movements and urination.

Figure 1:
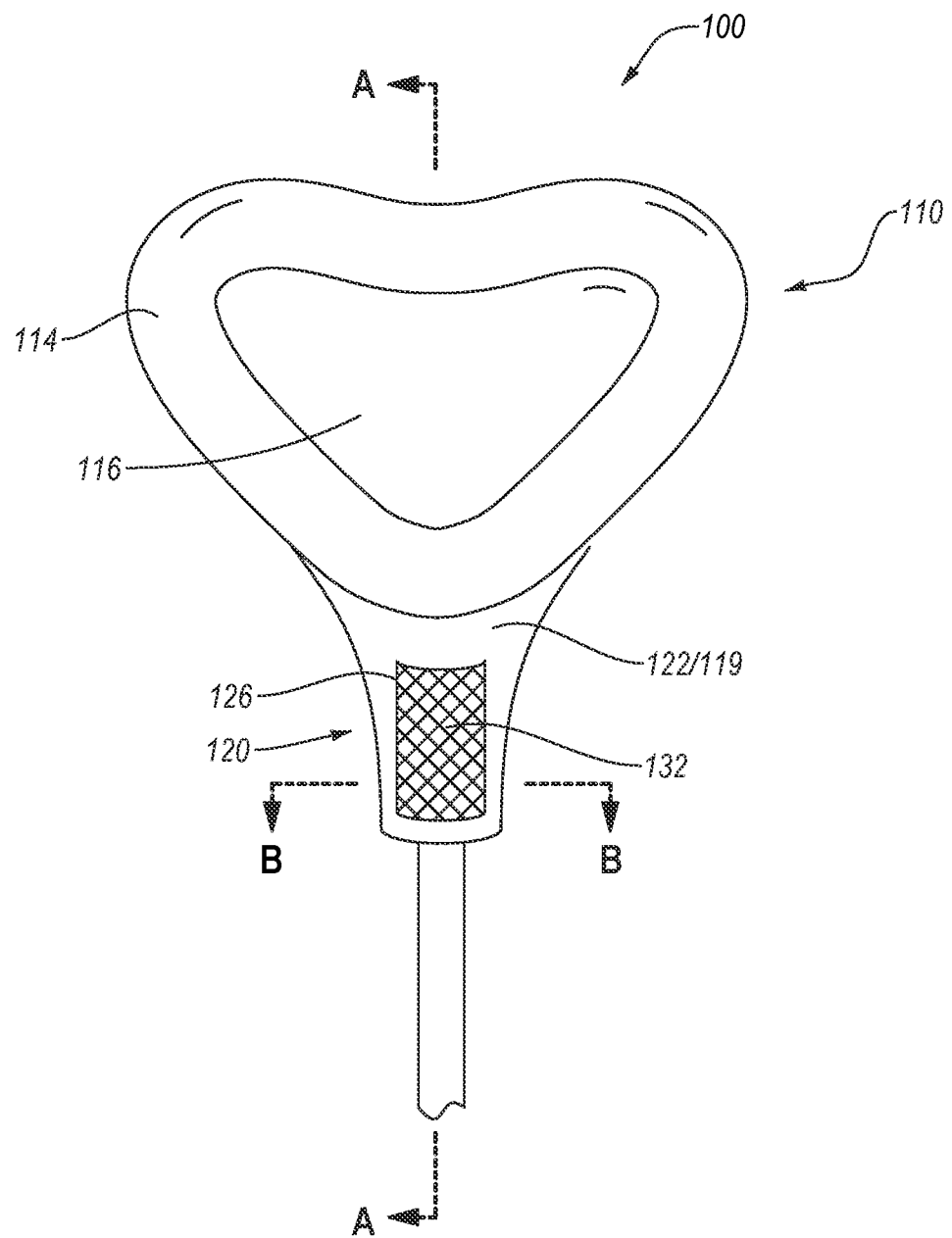
FIG. 1 is a front view of a bodily waste collection apparatus, according to an embodiment.
Figure 2:
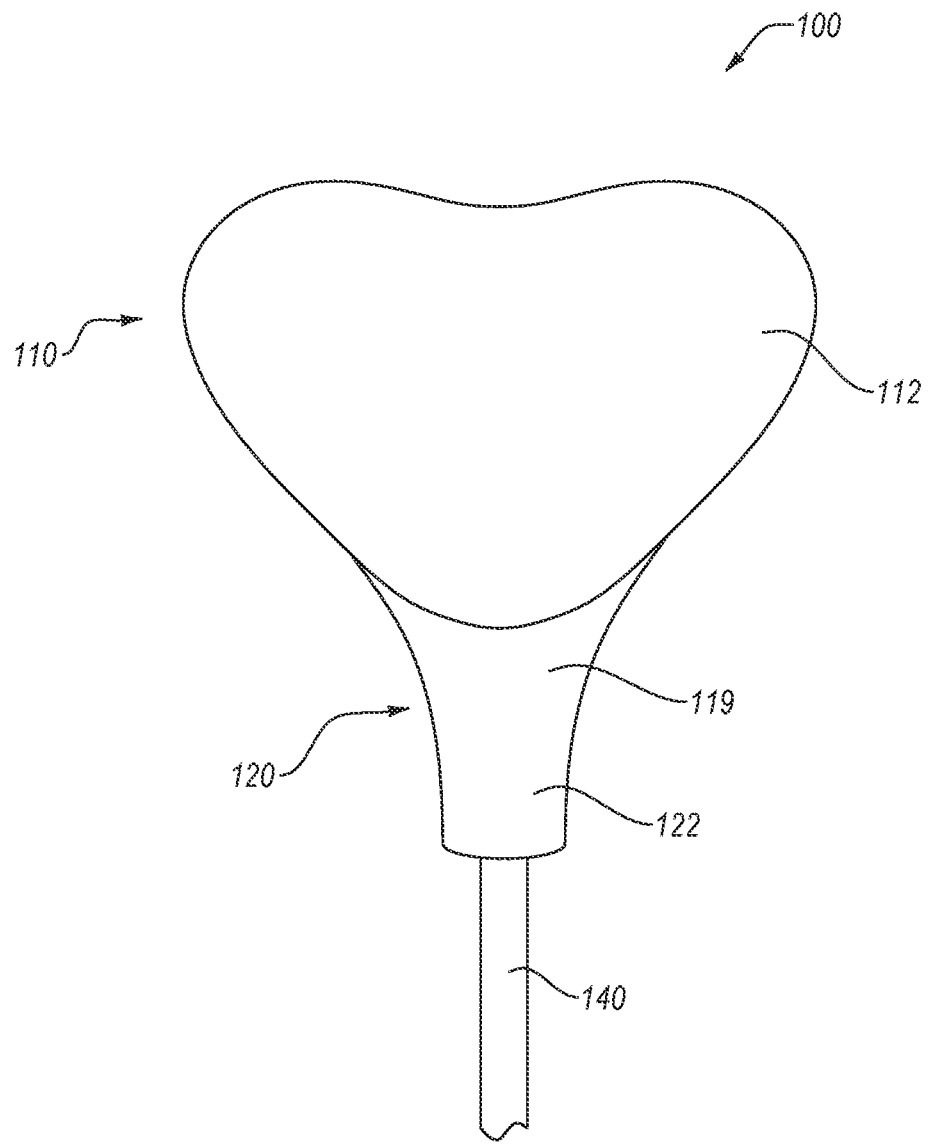
FIG. 2 is a back view the bodily waste collection apparatus of FIG. 1, according to an embodiment.
Figure 3A:
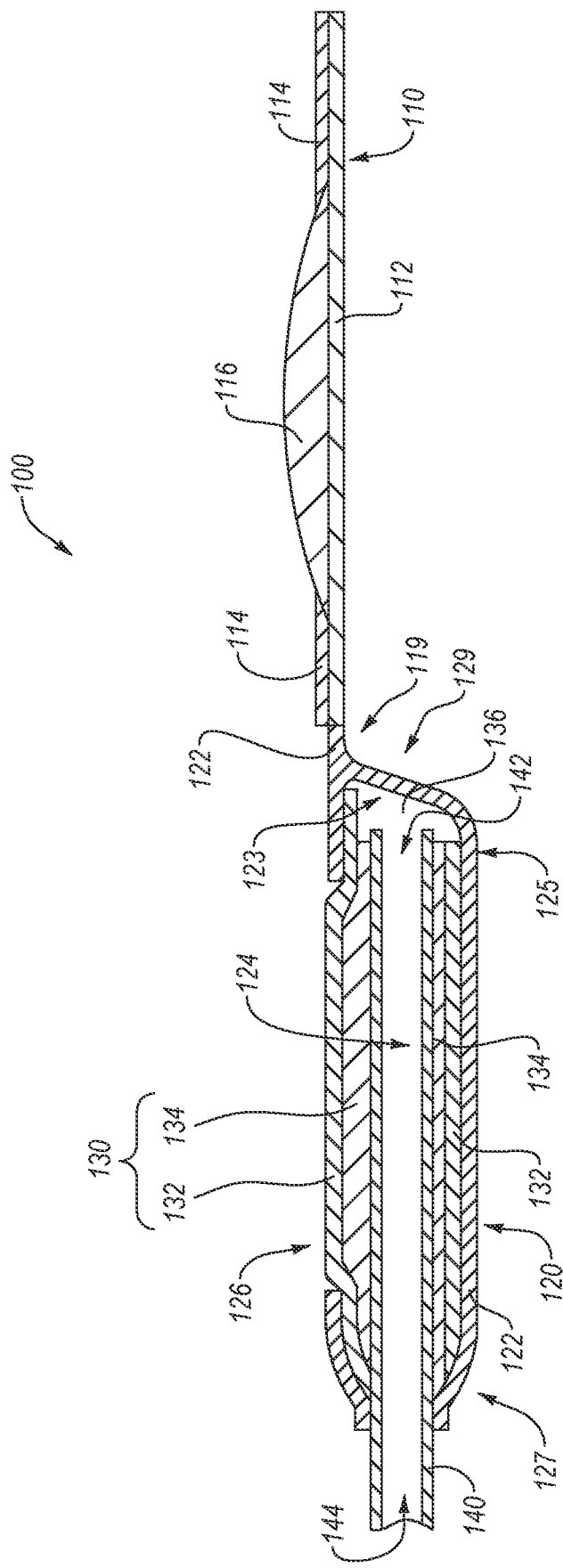
FIGS. 3A-3C are cross-sectional views of the bodily waste collection device of FIG. 1 taken along the plan A-A, according to various embodiments.

FIG. 1 is a front view of a bodily waste collection apparatus 100, according to an embodiment. FIG. 2 is a back view of a bodily waste collection apparatus 100 of FIG. 1, according to an embodiment. FIG. 3A is a side cross-sectional view of the bodily waste collection apparatus 100 of FIG. 1 viewed along the plane A-A, according to an embodiment. The bodily waste collection apparatus 100 includes a sacral pad 110 and a bodily waste collection device 120 attached thereto. The sacral pad 110 attaches to a wearer over the sacrum of the wearer. The bodily waste collection device 120 extends from the sacral pad 110 toward the wearer's anus. For example, after the sacral pad 110 is attached to the wearer, the bodily waste collection device 120 may be positioned adjacent to the wearer's anus, such that bodily waste expelled from the wearer contacts the bodily waste collection device 120.

The sacral pad 110 includes padding material 116 in a central region thereof and an adhesive 114 disposed around the padding material 116. The sacral pad 110 includes backing material 112. The backing material 112 may include a natural fibers, polymers, or combinations thereof. For example, the backing material 112 may include a flexible bandage material having a cotton-polymer blend of materials. In some examples, the backing material 112 may include a plastic strip or body. Suitable natural materials may include cotton, linen, silk, wool, rubber, or the like. Suitable polymer materials may include one or more of polyamides (e.g., Nylon), polyvinyl chloride, polyethylene, polyurethane, latex, silicone, or the like. In some examples, the backing material 112 may be at least partially fluid impermeable. The backing material 112 is sized and shaped to at least partially cover the sacral region of a wearer, with the outermost extend of the backing material 112 being surrounding the wearer's sacrum.

The padding material 116 and adhesive 114 are disposed on the wearer-facing side of the backing material 112. The padding material 116 may be disposed in an interior of the sacral pad 110 with the adhesive 114 extending therearound. In some examples, the sacral pad 110 may be generally heart-shaped with the padding material 116 being disposed in an interior of the sacral pad 110 and the adhesive 114 extending therearound. The sacral pad 110 may be any shape, such as circular, prismatic, rounded, or the like. The adhesive maintains the positioning of the sacral pad 110 on the wearer and the padding material 116 provides padding to prevent bedsores from forming on the sacrum of the wearer.

The padding material 116 may include any padding, such as a natural materials (e.g., fibers), polymer material (e.g., fibers, foam, or hydrogel), or combinations thereof. For example, the padding may include spun plastic fibers (e.g., Nylon), natural fibers (e.g., cotton), polymer foam (e.g., polyurethane), a hydrogel, or combinations of the foregoing. The padding material 116 may have a covering thereover, such as a perforated or otherwise breathable covering over at least a portion of the padding material. The padding material 116 may be located in a position on the backing material 112 expected to be positioned directly over the sacrum of the wearer during use. The padding material 116 may be at least 1 mm thick, such as 1 mm to 2.5 cm, 1 mm to 1 cm, 1 cm to 2 cm, less than 2.5 cm, less than 2 cm, less than 1.5 cm, or more than 2 cm.

The adhesive 114 may be disposed around the padding material 116 on the wearer facing side of the backing material 112. The adhesive 114 may include a medical adhesive or any other adhesive that is safe to use against the skin of humans, such as acrylate adhesives (e.g., methacrylates, epoxy diacrylates, or cyanoacrylate adhesives), silicone adhesives, hydrogels, or the like. In some examples, the adhesive 114 may additionally or alternatively be disposed on the padding material 116. The adhesive 114 may be disposed on the backing material 112 with a width of at least about 0.5 cm inward from the outer periphery of the sacral pad 110, such as 0.5 cm to 5 cm, 0.5 cm to 2 cm, 2 cm to 4 cm, 3 cm to 5 cm, less than 5 cm, or less than 2.5 cm.

The sacral pad 110 is sized and shaped to be attached to a wearer over the sacrum of the wearer and the bodily waste collection device 120 is sized and shaped to be disposed on over the anus of the wearer when the sacral pad 110 is attached to the wearer over the sacrum.

The bodily waste collection device 120 attached to a lower portion of the sacral pad 110. For example, the bodily waste collection device 120 may be attached to (e.g., welded, adhered, fastened, or otherwise affixed to) or integrally formed with the sacral pad 110. The bodily waste collection device 120 includes a fluid impermeable casing 122 defining an interior region therein, a permeable material 130 at least partially disposed in the interior region, and a conduit 140 disposed within the bodily waste collection device 120. The bodily waste collection device 120 receives bodily waste on the permeable material 130. At least the liquid waste (e.g., urine, liquid or semi-liquid stool) may be removed into the bodily waste collection device 120 via the permeable material 130.

The fluid impermeable casing 122 may at least partially defines the interior region 124 and an opening 126. For example, the inner surface(s) 123 of the fluid impermeable casing 122 at least partially defines the interior region 124 within the bodily waste collection device 120. The fluid impermeable casing 122 at least temporarily retains the fluid(s) in the interior region 124. The fluid impermeable casing 122 may be formed of any suitable fluid impermeable material(s), such as a fluid impermeable polymer, a metal film, natural rubber, another suitable material, or combinations thereof. For example, the fluid impermeable casing 122 may include silicone, polypropylenes, polyethylenes, polyethylene terephthalates, polystyrenes, polyurethanes, polycarbonates, polyamides, polyesters, polyacrylates, polychloroprene, vinyl, polyvinyl chloride, poly(vinyl imidazole), thermoplastic elastomer(s), latex, silanes (e.g., an halogenated alkyl silane), perfluorinated polymers, polytetrafluoroethylene (PTFE), chlorosulphonate polyolefins, polyethylene oxide, blends or copolymers of any of the foregoing, or any other fluid impermeable polymer. As such, the fluid impermeable casing 122 substantially prevents the fluid(s) from passing therethrough.

The opening 126 allows the interior region 124 to be in fluid communication with the external environment outside of the bodily waste collection device 120. The opening 126 is on the wearer-facing (e.g., upper) surface of the bodily waste collection device 120. Accordingly, the adhesive 114 attaches the sacral pad 110 to the wearer and the opening 126 of the bodily waste collection device 120 is positioned over the anus of the wearer.

The opening 126 may be elongated, extending from a first location near the first end region 127 of the bodily waste collection device 120 to the a second location near the second end region 129. The opening 126 may be larger than the anus of the wearer. The opening 126 may exhibit an elongated shape because the space in the gluteal cleft of a wearer is relatively narrow, thereby only permitting the flow of bodily waste (e.g., feces) along a path that corresponds to the elongated shape of the opening 126 (e.g., longitudinally extending opening). The opening 126 in the fluid impermeable casing 122 may exhibit a length that is measured along the longitudinal axis of the bodily waste collection device 120 that may be at least about 10% of the length of the bodily waste collection device 120, such as about 25% to about 50%, about 40% to about 60%, about 50% to about 75%, about 65% to about 85%, or about 75% to about 95% of the length of the bodily waste collection device 120. The opening 126 in the fluid impermeable casing 122 may exhibit a width that is measured transverse to the longitudinal axis of the bodily waste collection device 120 and may be at least about 10% of the circumference of the bodily waste collection device 120, such as about 25% to about 50%, about 40% to about 60%, about 50% to about 75%, about 65% to about 85%, or about 75% to about 100% of the circumference of the bodily waste collection device 120. The opening 126 may exhibit a width that is greater than 20% of the circumference of the bodily waste collection device 120 since the vacuum (e.g., suction) through the conduit 140 pulls fluid of the bodily waste through the permeable material 130 and into the conduit 140. The opening 126 may be longitudinally oriented (e.g., having a major axis parallel to the longitudinal axis of the device 120). In some examples (not shown), the opening 126 may be laterally oriented (e.g., having a major axis perpendicular to the longitudinal axis of the device 120).

The permeable material 130 at least partially fills the interior region 124. The permeable material 130 may extend across at least a portion (e.g., all) of the opening 126. At least a portion of the permeable material 130 may be exposed to an environment outside of the interior region 124 through the opening 126.

The permeable material 130 may be configured to wick any fluid away from the opening 126, thereby preventing the fluid from escaping the interior region 124. The permeable material 130 may also wick the fluid generally inwards in the interior region 124. The permeable material 130 includes a fluid permeable sheath 132 and a fluid permeable base 134 disposed at least partially under the fluid permeable sheath 132.

The fluid permeable sheath 132 may include any porous material or a material that may wick the fluid. For example, the fluid permeable sheath 132 may include fabric, such as a gauze (e.g., a silk, linen, or cotton gauze), another soft fabric, or another smooth fabric. The fluid permeable sheath 132 may include spun plastic fibers (e.g., nylon), such as a spun plastic mat or bed. Forming the fluid permeable sheath 132 from gauze, soft fabric, and/or smooth fabric may reduce chaffing caused by the bodily waste collection device 120.

The bodily waste collection device 120 may include the fluid permeable sheath 132 disposed in the interior region 124. The fluid permeable sheath 132 may extend across at least a portion (e.g., all) of the opening 126. The fluid permeable sheath 132 may be composed to wick any fluid in contact therewith inwardly away from the opening 126, thereby preventing the fluid from escaping the bodily waste collection device 120. Accordingly, liquid or semi-liquid bodily waste may be collected and removed from the wearer (e.g., via one or more of wicking, gravity, or vacuum force) thereby limiting or preventing the fluid therein from contaminating the wearer's clothing, bedding, or skin.

The fluid permeable base 134 is disposed in the interior region 124. The fluid permeable base 134 is composed to support the fluid permeable sheath 132 since the fluid permeable sheath 132 may be formed from a foldable, flimsy, or otherwise easily deformable material. For example, the fluid permeable base 134 may be positioned such that the fluid permeable sheath 132 is disposed between the fluid permeable base 134 and the fluid impermeable casing 122. As such, the fluid permeable base 134 may support and maintain the position of the fluid permeable sheath 132 thereon. The fluid permeable base 134 may include any material that may wick the fluid, such as any of the fluid permeable sheath materials disclosed herein. For example, the fluid permeable base 134 may be formed from any fluid porous material that is less deformable than the fluid permeable sheath 132, such as any of the materials disclosed herein for the fluid permeable sheath 132, in a more dense or rigid form. In some examples, the fluid permeable base 134 may include a porous polymer (e.g., nylon, polyester, polyurethane, polyethylene, polypropylene, etc.) structure, an open cell foam, or spun plastic fibers (e.g., nylon fibers). In some examples, the fluid permeable sheath 132 may include gauze and the fluid permeable base 134 may include spun nylon fibers. In some examples, the fluid permeable base 134 may be formed from fabric, felt, gauze, open cell foam, or combinations thereof. In some examples, the fluid permeable base 134 may be formed from a natural material, such as cotton, wool, silk, or combinations thereof. In such examples, the material may have a coating to prevent or limit absorption of fluid into the fibers of the material, such as a water repellent coating. In some examples, the fluid permeable base 134 may be omitted from the bodily waste collection device 120. In some examples, the fluid permeable sheath 132 may be optional. For example, the permeable material 130 may include only the fluid permeable base 134.

The fluid permeable base 134 may have a greater permeability or a greater ability to wick fluids than the fluid permeable sheath 132, such as to move the fluid inwardly from the outer surface of the bodily waste collection device 120. In some examples, the permeability or the wicking ability of the fluid permeable base 134 and the fluid permeable sheath 132 may be substantially the same.

The fluid permeable sheath 132 and the fluid permeable base 134 may at least substantially completely fill the portions of the interior region 124 that are not occupied by the conduit 140. In another example, the fluid permeable sheath 132 and the fluid permeable base 134 may not substantially completely fill the portions of the interior region 124 that are not occupied by the conduit 140. In such an example, the bodily waste collection device 120 includes a reservoir 136 in the interior region 124.

As illustrated in FIG. 3A, the conduit 140 may be at least partially disposed in the interior region 124. The conduit 140 includes an inlet 142 at the second end region 129 and an outlet 144 at the first end region 127 positioned downstream from the inlet 142. The conduit 140 may extend into the interior region 124 to any point therein. For example, the conduit 140 may be inserted into the interior region 124 at the first end region 127 of the bodily waste collection device 120 and extend therethrough to the second end region 129 of the bodily waste collection device 120. The conduit 140 may extend into the fluid impermeable casing 122 from the first end region 127 through to the second end region 129 (e.g., opposite the first end region 127) to a point proximate to the reservoir 136 such that the inlet 142 is in fluid communication with the reservoir 136. Such examples may be particularly useful when the second end region 129 is expected to be at a gravimetrically low point of the bodily waste collection device 120 during use.

In some examples (not shown), the conduit 140 may enter the interior region 124 in the second end region 129 and the inlet 142 of the conduit 140 may be disposed in the second end region 129 (e.g., in the reservoir 136 or flush with fluid impermeable casing 122). The fluid collected in the reservoir 136 may be removed from the interior region 124 via the conduit 140. In some examples, the inlet 142 may be disposed at the end of the fluid permeable base 134 in the second end region 129, such as flush with the end of the fluid permeable base 134. In some examples, the inlet 142 may be disposed within the fluid permeable base 134 such between first end region 127 and the second end region 129. The bodily waste collection device 120 may be at least partially rigid around the reservoir 136, such as one or more the fluid impermeable casing 122 or permeable material 130 being at least partially rigid to prevent the bodily waste collection device 120 from collapsing. By preventing the bodily waste collection device 120 from collapsing in at least the region thereof having the reservoir 136, the bodily waste collection device 120 allows fluids to flow into the reservoir 136.

The conduit 140 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In some examples, the conduit 140 may include silicon or latex. In some examples, the conduit 140 may include one or more portions that are resilient, such as to by having one or more of a diameter or wall thickness that allows the conduit 140 to be flexible. In some examples, the conduit 140 may be frosted or opaque (e.g., black) to obscure visibility of the fluid(s) therein.

The bodily waste collection device 120 may be operably coupled to a fluid storage container and a vacuum source via the conduit 140. For example, the conduit 140 fluidly connects the interior region 124 with the fluid storage container or the vacuum source (via the fluid storage container). Accordingly, fluids may be removed from the interior region 124 via the conduit 140.

The bodily waste collection apparatus 100 includes a connecting portion 119 that connects the bodily waste collection device 120 to the sacral pad 110. For example, the bodily waste collection device 120, such as the fluid impermeable casing 122, may form the at least part of the connecting portion 119. Alternatively or additionally, a lower portion of the sacral pad 110 may form at least part of the connecting portion 119. The length of the connecting portion 119 may be selected to match the anatomical features of the wearer, such as to allow the opening 126 to be positioned over the anus of the wearer. Accordingly, the connecting portion 119 may be any selected length.

Figure 3B:
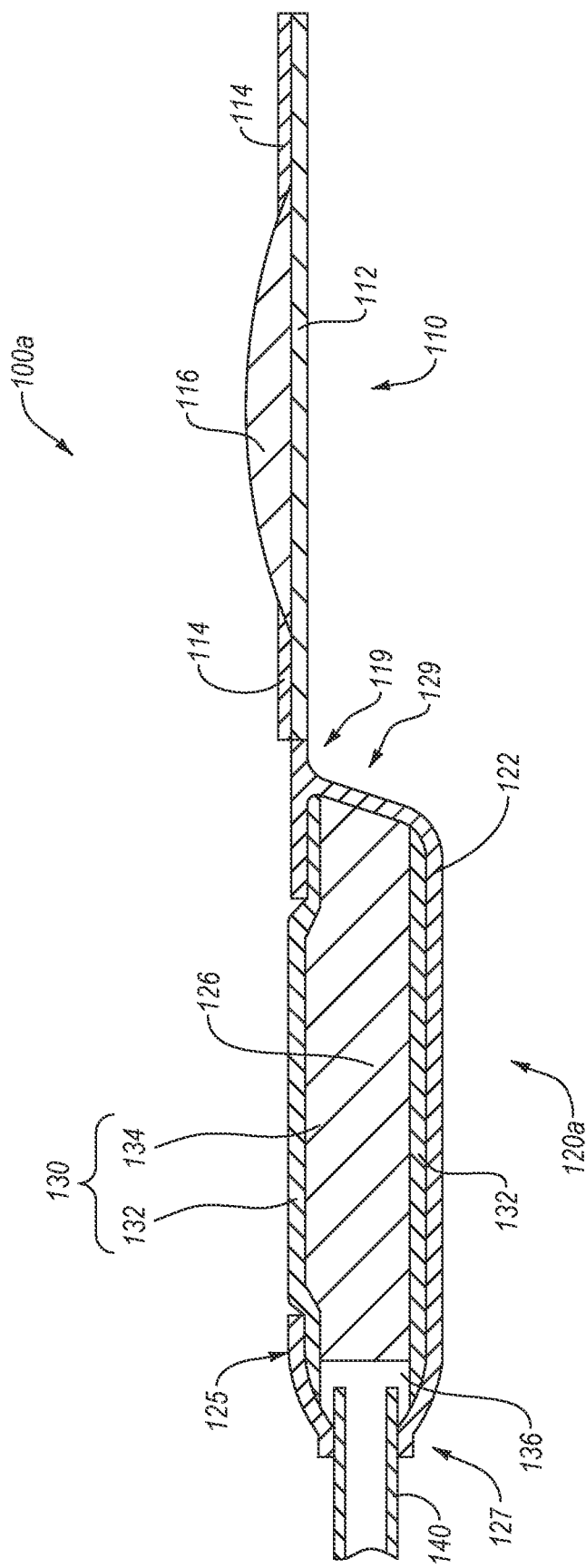
Figure 3C:
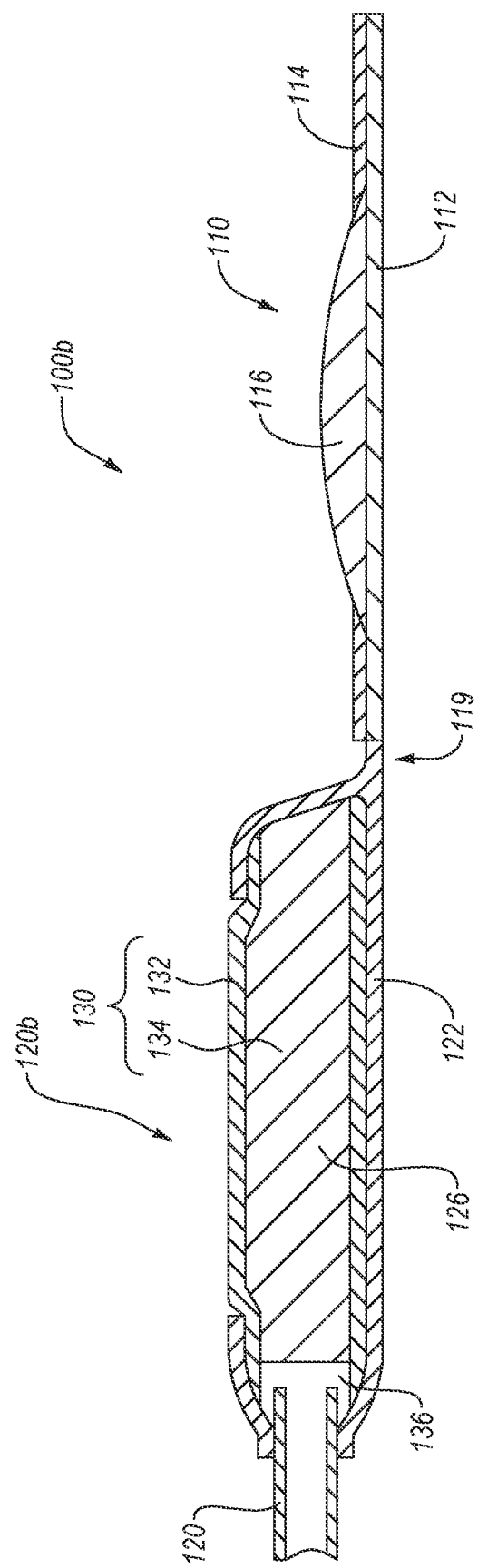

While depicted in FIG. 3A as having the reservoir 136 in the second end region 129, some embodiments of the bodily waste collection device 120 may have the reservoir 136 in the first end region 127. FIG. 3B is a cross-sectional view of the bodily waste collection device of FIG. 1 taken along the plan A-A, according to an embodiment. As shown in FIG. 3B, the conduit 140 may not be disposed in the interior region 124 in the second end region 129. Rather, the bodily waste collection device 120a of the bodily waste collection apparatus 100a may have a conduit 140 that enters in the first end region 127 and terminates in the first end region 127. In such examples, the reservoir 136 is in the first end region 127. In such examples, the permeable material 130 may be disposed in the central portion of the interior region 124 (e.g., where the conduit 140 is disposed within the interior region 124 in FIG. 3A), and extend therethrough to at least partially fill the interior region 124 in second end region 129. Such an example of a bodily waste collection apparatus 100a, may be utilized where the first end region 127 is expected to be positioned at a gravimetrically low point of the bodily waste collection device during use.

As shown in FIGS. 3A and 3B, the interior region 124 may be positioned below the plane of the backing material 112 when the bodily waste collection apparatus is flattened. In some examples, the interior region 124 may be positioned above the plane of the backing material 112 when the bodily waste collection apparatus is flattened. FIG. 3B is a cross-sectional view of the bodily waste collection device of FIG. 1 taken along the plan A-A, according to an embodiment. The bodily waste collection device 120b of the bodily waste collection apparatus 100b may be below the plane of the backing material 112 when the bodily waste collection apparatus 100b is flattened. Such configuration may allow the bodily waste collection device 120b to be more easily disposed in the intergluteal cleft of the wearer than configurations where the bodily waste collection device 120 is disposed below the plane of the backing material 112 when the bodily waste collection apparatus 100 is flattened.

Further examples (not shown) may be utilized, such as where the bodily waste collection device 120 is disposed in plane with (e.g., above and below) the plane of the backing material 112 when the bodily waste collection apparatus 100 is flattened.

While shown as separate materials in FIGS. 1-3C, in some examples, the backing material 112 and the fluid impermeable casing 122 may be the same material.

Figure 4:
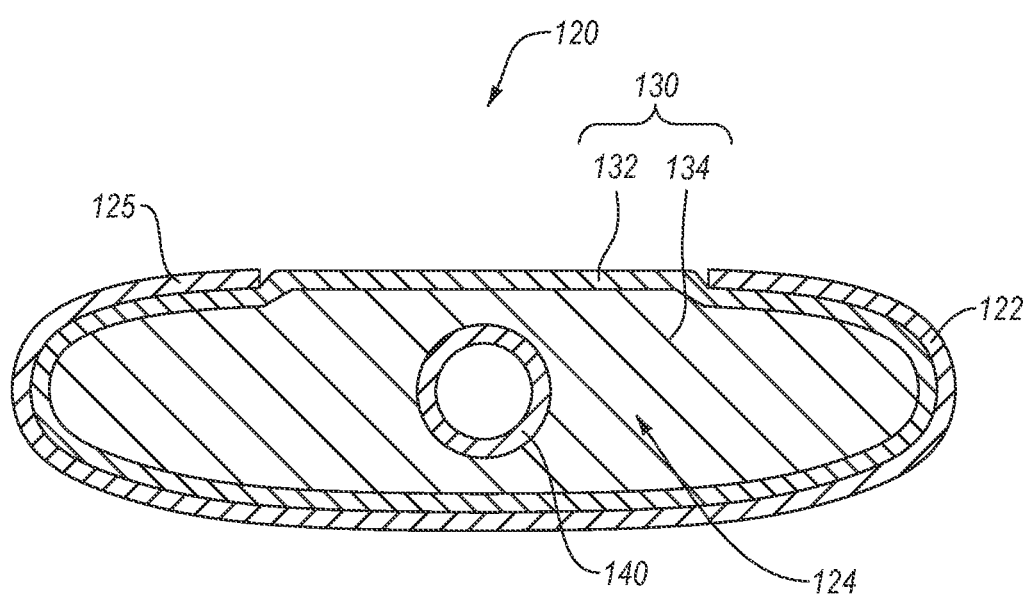
FIG. 4 is a cross-sectional view of the bodily waste collection device of FIG. 1 taken along the plane B-B, according to an embodiment.

The bodily waste collection device 120-120b may have any cross-sectional shape when viewed along the longitudinal axis. FIG. 4 is a cross-sectional view of the bodily waste collection device 120 of FIG. 1 taken along the plane B-B, according to an embodiment. The bodily waste collection device 120 is sized and shaped to at least partially fit within the intergluteal cleft when the sacral pad is attached to the wearer over the sacrum. As shown, the bodily waste collection device 120 may be tubular (ignoring the opening therein). For example, the fluid impermeable casing 122 may be substantially cylindrical, oblong, prismatic, a flattened tube, or any other extruded shape. The fluid impermeable casing 122 may be sized to fit between the legs of a wearer. During use, an outer surface 125 of the fluid impermeable casing 122 may at least partially contact the wearer. In some examples, the bodily waste collection device 120 and components thereof may be at least partially malleable to allow a user to reshape the bodily waste collection device 120 by applying external force thereto.

The bodily waste collection device 120 may be at least 1 cm thick, such as 1 cm to 5 cm, 1 cm to 3 cm, 2 cm to 4 cm, 3 cm to 5 cm, less than 5 cm, or less than 3 cm. The bodily waste collection device 120 may be at least 2 cm wide, such as 2 cm to 10 cm, 2 cm to 5 cm, 4 cm to 8 cm, 6 cm to 10 cm, less than 10 cm, or less than 6 cm. The bodily waste collection device 120 may be at least 6 cm long, such as 6 cm to 20 cm, 6 cm to 10 cm, 10 cm to 15 cm, 15 cm to 20 cm, less than 20 cm, or less than 15 cm.

Figure 5:
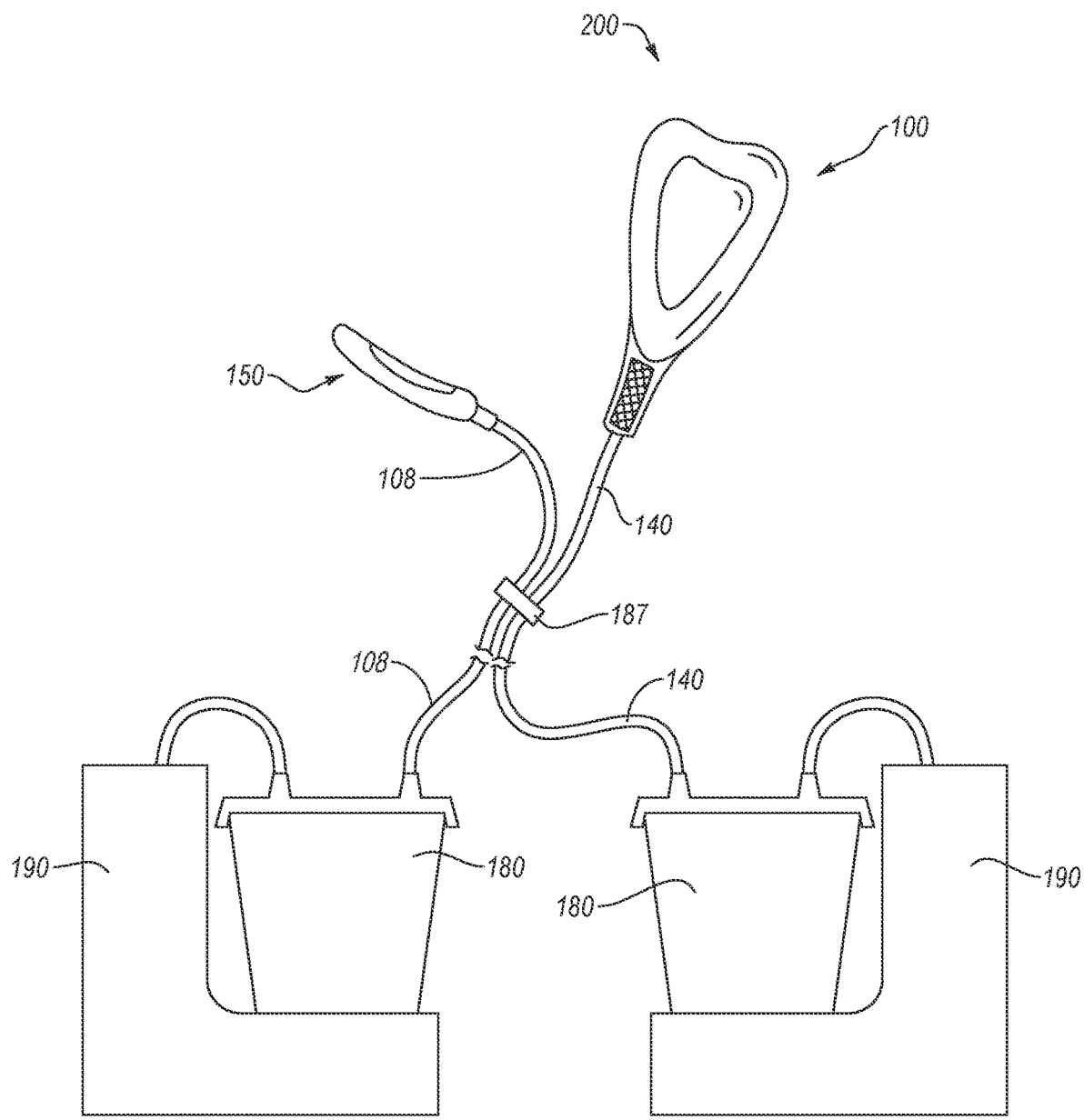
FIG. 5 is a schematic of a system for collecting bodily waste, according to an embodiment.

FIG. 5 is a schematic of a system 200 for collecting bodily waste, according to an embodiment. The system 200 includes the bodily waste collection apparatus 100, at least one the fluid storage container 180, at least one the vacuum source 190, and optionally, a fluid collection device 150. The bodily waste collection apparatus 100 may be fluidly connected to one or more of the at least one fluid storage container 180 or the at least one vacuum source 190 via the conduit 140. Accordingly, at least the fluids from bodily waste may be pulled through the bodily waste collection apparatus 100 into the fluid storage container 180 by one or more of gravity or suction provided by the at least one vacuum source 190.

The bodily waste collection apparatus 100 of the system 200 may include a fluid collection device 150 for storing fluid(s), such as urine, collected therein. For example, the fluid collection device 150 may be attached or tethered to the bodily waste collection apparatus 100 by an attachment 187 holding conduits 140 and 108 for the respective apparatus and device. The conduit 140 attached to the bodily waste collection apparatus 100 and the additional conduit 108 attached to the fluid collection device 150 are coupled to each other by the attachment 187.

The fluid collection device 150 may be operably coupled to one or more of the at least one fluid storage container 180 or the at least one vacuum source 190 via the additional conduit 108. Accordingly, urine may be collected in the fluid collection device 150 and pulled into the fluid storage container 180 by one or more of gravity or suction provided by the at least one vacuum source 190.

In some examples, the at least one fluid storage container 180 includes a first fluid storage container and a second storage container. In such examples, the first fluid storage container is fluid connected to the bodily waste collection device 120 and the second fluid storage container is fluidly connected to the fluid collection device 150. In such examples, the first fluid storage container and the second fluid storage container may be fluidly connected to the at least one vacuum source 190, such as a single vacuum source or separate vacuum sources. For example, the at least one vacuum source 190 may include a first vacuum source fluidly connected to the first fluid storage container and a second vacuum source fluidly connected to the second fluid storage container.

Figure 6:
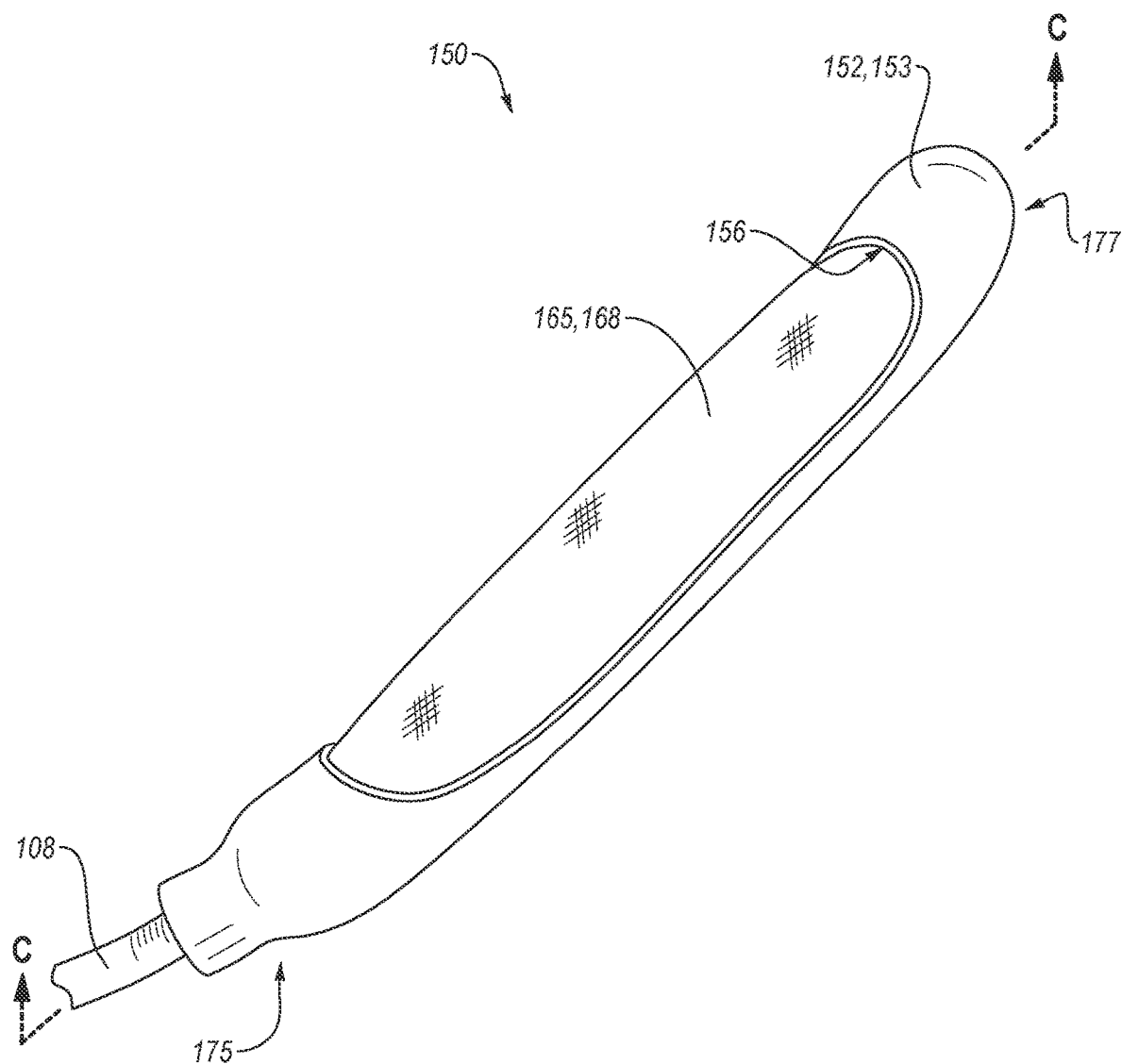
FIG. 6 is an isometric view of a fluid collection device, according to an embodiment.
Figure 7:
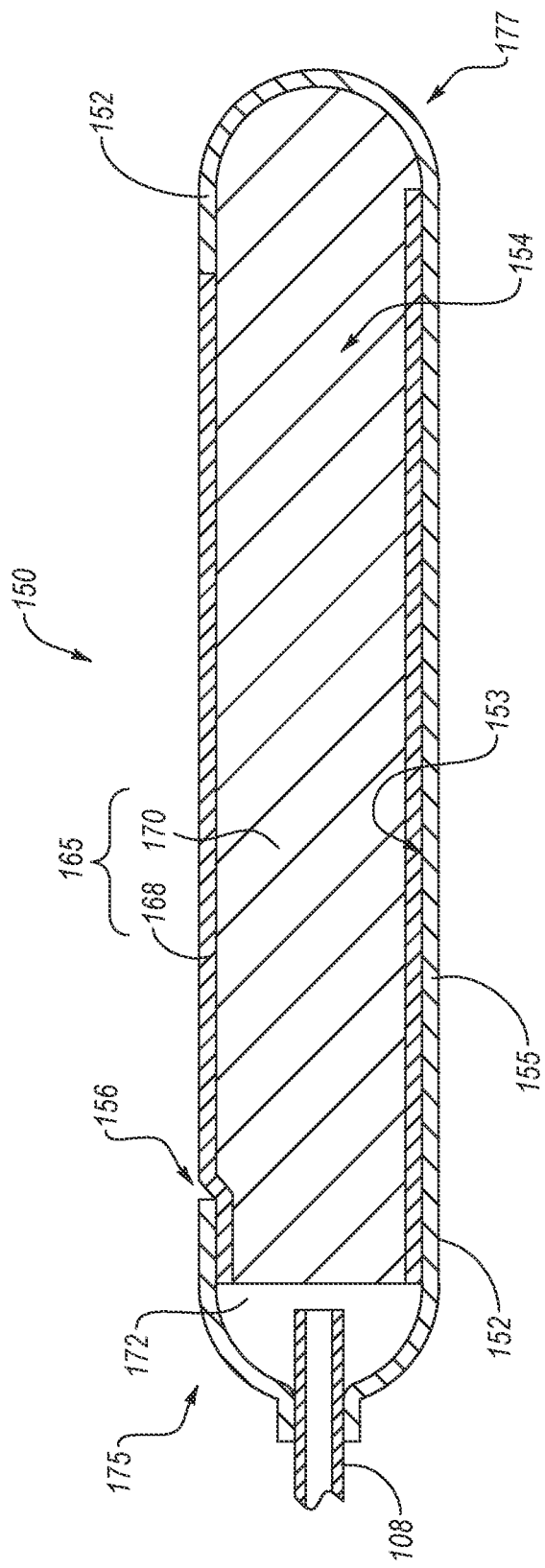
FIG. 7 is a cross-sectional view of the fluid collection device of FIG. 6 taken along the plane C-C, according to an embodiment.

FIG. 6 is an isometric view of a fluid collection device, according to an embodiment. FIG. 7 is a cross-sectional view of the fluid collection device of FIG. 6 taken along the plane C-C, according to an embodiment. The fluid collection device 150 is sized, shaped, and composed to collect urine from the urethra of a wearer. The fluid collection device 150 includes a fluid impermeable barrier 152 defining a cavity 154 therein, a porous material 165 disposed in the cavity 154, and an additional conduit 108 disposed in the cavity 154. The porous material 165 may be exposed to the external environment via the opening 156 in the fluid impermeable barrier 152. During use, the fluid collection device 150 may be positioned over the urethra of the wearer and urine may be received into the fluid collection device 150 by the porous material 165 via the opening 156. The urine may be removed from the fluid collection device 150 via the (additional) conduit 108 disposed within the cavity 154.

The fluid impermeable barrier 152 at least partially defines the cavity 154 (e.g., interior region) and opening 156. For example, the inner surface(s) 153 of the fluid impermeable barrier 152 at least partially defines the cavity 154 within the fluid collection device 150. The fluid impermeable barrier 152 at least temporarily retains the fluid(s) in the cavity 154. The fluid impermeable barrier 152 may be formed of any of the materials for the fluid impermeable casing disclosed herein. The fluid impermeable barrier 152 may be formed of any suitable fluid impermeable material(s), such as a fluid impermeable polymer (e.g., silicone, polypropylene, polyethylene, polyethylene terephthalate, thermoplastic elastomer(s), a polycarbonate, etc.), a metal film, natural rubber, another suitable material, or combinations thereof. As such, the fluid impermeable barrier 152 substantially prevents the fluid(s) from passing therethrough. In an example, the fluid impermeable barrier 152 may be air permeable and liquid impermeable. In such an example, the fluid impermeable barrier 152 may be formed of a hydrophobic material that defines a plurality of pores that are air permeable but not liquid permeable. In an example, one or more portions of at least an outer surface of the fluid impermeable barrier 152 may be formed from a soft and/or smooth material, thereby reducing chaffing.

In some examples, the fluid impermeable barrier 152 may be tubular (ignoring the opening), such as substantially cylindrical (as shown), oblong, prismatic, flattened tube, or any other extruded shape. The fluid impermeable barrier 152 may be sized to fit between the legs of a wearer. During use, an outer surface 155 of the fluid impermeable barrier 152 may at least partially contact the wearer, such as the thighs of the wearer.

The opening 156 provides an ingress route for fluids to enter the cavity 154. The opening 156 may be defined by the fluid impermeable barrier 152, such as by an inner edge of the fluid impermeable barrier 152. For example, the opening 156 is formed in and extends through the fluid impermeable barrier 152, from the outer surface 155 to the inner surface 153, thereby enabling fluid(s) to enter the cavity 154 from outside of the fluid collection device 150. The opening 156 may be located and shaped to be positioned adjacent to a wearer's urethra while the device is in use. At least a portion of porous material(s) disposed in the cavity 154 may be exposed through the opening 156 to allow fluids to move inwardly into the cavity 154, such as via one or more of permeation, suction, or wicking.

The fluid collection device 150 may be positioned proximate to the urethra and urine may enter the cavity 154 via the opening 156. When in use, the opening 156 may be elongated, extending from a first location below the urethra to a second location above the urethra (e.g., at or near the top of the vaginal opening or the pubic region). The opening 156 may exhibit an elongated shape because the space between the legs of a wearer is relatively narrow when the legs of the wearer are closed, thereby only permitting the flow of the fluid(s) along a path that corresponds to the elongated shape of the opening 156 (e.g., longitudinally extending opening). The opening 156 in the fluid impermeable barrier 152 may exhibit a length that is measured along the longitudinal axis of the fluid collection device 150 that may be at least about 10% of the length of the fluid collection device 150, such as about 25% to about 50%, about 40% to about 60%, about 50% to about 75%, about 65% to about 85%, or about 75% to about 95% of the length of the fluid collection device 150.

The opening 156 in the fluid impermeable barrier 152 may exhibit a width that is measured transverse to the longitudinal axis of the fluid collection device 150 and may be at least about 10% of the circumference of the fluid collection device 150, such as about 25% to about 50%, about 40% to about 60%, about 50% to about 75%, about 65% to about 85%, or about 75% to about 100% of the circumference of the fluid collection device 150. The opening 156 may exhibit a width that is greater than 50% of the circumference of the fluid collection device 150 since the vacuum (e.g., suction) through the additional conduit 108 pulls the fluid through the porous material 165 and into the additional conduit 108. The additional conduit 108 may be similar or identical to the conduit 140, in one or more aspects. The opening 156 may be longitudinally oriented (e.g., having a major axis parallel to the longitudinal axis of the device 150). In some examples (not shown), the opening 156 may be laterally oriented (e.g., having a major axis perpendicular to the longitudinal axis of the device 150).

The fluid collection device 150 includes the porous material 165 disposed in the cavity 154. The porous material 165 may extend across at least a portion (e.g., all) of the opening 156. At least a portion of the porous material 165 may be exposed to an environment outside of the cavity 154 through the opening 156. The porous material 165 may wick any fluid away from the opening 156, thereby preventing the fluid from escaping the cavity 154. The permeable properties of the porous material 165 referred to herein may be wicking as disclosed above with respect to the permeable material 130. The porous material 165 may be less porous than the permeable material 130. Accordingly, the permeable material 130 (FIG. 3A) may allow for more solids to be moved therethrough than the porous material 165.

The porous material 165 may include one or more of a fluid permeable membrane 168 or a fluid permeable support 170. The fluid permeable membrane 168 may include any porous material or a material that may wick the fluid. For example, the fluid permeable membrane 168 may include fabric, such as a gauze (e.g., a silk, linen, or cotton gauze), another soft fabric, or another smooth fabric. The fluid permeable membrane 168 may include spun plastic fibers (e.g., nylon), such as a spun plastic mat or bed. Forming the fluid permeable membrane 168 from gauze, soft fabric, and/or smooth fabric may reduce chaffing caused by the fluid collection device 150.

The fluid permeable membrane 168 is disposed in the cavity 154. The fluid permeable membrane 168 may extend across at least a portion (e.g., all) of the opening 156. The fluid permeable membrane 168 may wick fluid inwardly away from the opening 156, thereby preventing fluid from escaping the cavity 154.

The porous material 165 of the fluid collection device 150 may include the fluid permeable support 170 disposed in the cavity 154. The fluid permeable support 170 is composed to support the fluid permeable membrane 168 since the fluid permeable membrane 168 may be formed from a foldable, flimsy, or otherwise easily deformable material. For example, the fluid permeable support 170 may be positioned such that the fluid permeable membrane 168 is disposed between the fluid permeable support 170 and the fluid impermeable barrier 152. As such, the fluid permeable support 170 may support and maintain the position of the fluid permeable membrane 168 thereon. The fluid permeable support 170 may include any material that may wick the fluid, such as any of the fluid permeable membrane materials disclosed herein. For example, the fluid permeable support 170 may be formed from any fluid porous material that is less deformable than the fluid permeable membrane 168, such as any of the materials disclosed herein for the fluid permeable membrane 168, in a more dense or rigid form. In some examples, the fluid permeable support 170 may include a porous polymer (e.g., nylon, polyester, polyurethane, polyethylene, polypropylene, etc.) structure, an open cell foam, or spun plastic fibers (e.g., nylon fibers). In some examples, the fluid permeable membrane 168 may include gauze and the fluid permeable support may include spun nylon fibers. In some examples, the fluid permeable support 170 may be formed from fabric, felt, gauze, or combinations thereof. In some examples, the fluid permeable support 170 may be formed from a natural material, such as cotton, wool, silk, or combinations thereof. In such examples, the material may have a coating to prevent or limit absorption of fluid into the material, such as a water repellent coating. In some examples, the fluid permeable support 170 may be omitted from the fluid collection device 150. In some examples, the fluid permeable membrane 168 may be optional. For example, the porous material 165 may include only the fluid permeable support 170.

The fluid permeable support 170 may have a greater permeability or a greater ability to wick fluids than the fluid permeable membrane 168, such as to move the fluid inwardly from the outer surface of the fluid collection device 150. In some examples, the permeability or the wicking ability of the fluid permeable support 170 and the fluid permeable membrane 168 may be substantially the same.

The fluid permeable membrane 168 and the fluid permeable support 170 may at least substantially completely fill the portions of the cavity 154 that are not occupied by the additional conduit 108. In another example, the fluid permeable membrane 168 and the fluid permeable support 170 may not substantially completely fill the portions of the cavity 154 that are not occupied by the additional conduit 108. In such an example, the fluid collection device 150 includes a reservoir 172 (FIG. 7) in the cavity 154.

The conduit 140 extends into the cavity 154. As illustrated in FIG. 7, the additional conduit 108 may be at least partially disposed in the cavity 154. The additional conduit 108 (e.g., a drainage tube) includes an inlet an outlet positioned downstream from the inlet. The additional conduit 108 may extend into the cavity 154 to any point therein. For example, the additional conduit 108 may be inserted into the cavity 154 at the first end region 175 of the fluid collection device 150 and extend therethrough into the first end region 175 or to the second end region 177. As shown, the additional conduit 108 may extend into the fluid impermeable barrier 152 from the first end region 175 through to the reservoir 172 such that the inlet of the additional conduit 108 is in fluid communication with the reservoir 172. The fluid collected in the reservoir 172 may be removed from the cavity 154 via the additional conduit 108.

In some examples (not shown), the additional conduit 108 may enter the cavity 154 in the second end region 177 and the inlet of the additional conduit 108 may be disposed in the second end region 177. The reservoir 172 may be disposed in the second end region 177 in any of the embodiments disclosed herein. As shown, the inlet may be spaced from the end of the fluid permeable support 170 in the first end region 175. In some examples, the inlet may be disposed at the end of the fluid permeable support 170 in the first end region 175, such as flush with the end of the fluid permeable support 170. In some examples, the inlet may be disposed within the fluid permeable support 170 such between first end region 175 and the second end region 177.

The fluid impermeable barrier 152, the fluid permeable membrane 168 and the fluid permeable support 170 may be sized and shaped to have the additional conduit 108 at least partially disposed in the cavity 154. For example, at least one of the fluid permeable membrane 168 and the fluid permeable support 170 may be configured to form a space that accommodates the additional conduit 108. The fluid impermeable barrier 152 may define an aperture sized to receive the additional conduit 108. The additional conduit 108 may be disposed in the cavity 154 via the aperture. The aperture may be sized and shaped to form an at least substantially fluid tight seal against the additional conduit 108, thereby substantially preventing the fluid(s) from escaping the cavity 154. The fluid collected in the fluid collection device 150 may be removed from the cavity 154 via the additional conduit 108.

The porous material 165 (e.g., fluid permeable membrane 168 and the fluid permeable support 170) may not substantially completely fill the portions of the cavity 154 that are not occupied by the additional conduit 108. The fluid collection device 150 may include the reservoir 172 therein. As shown, the reservoir 172 is a substantially unoccupied portion of the cavity 154. The reservoir 172 may be defined between the fluid impermeable barrier 152 and the porous material 165 (e.g., one or both of the fluid permeable membrane 168 and the fluid permeable support 170). The fluid(s) emitted by the wearer may be wicked into the cavity 154 by the porous material 165 and may flow through the fluid permeable membrane 168 and/or fluid permeable support 170 to the reservoir 172. The fluid impermeable barrier 152 may retain the fluid(s) in the reservoir 172. The reservoir 172 may be located in a portion of the fluid collection device expected to be positioned in a gravimetrically low point of the fluid collection device when worn by a user. In such examples, the location of the inlet of the additional conduit 108 and the reservoir 172 at the gravimetrically low point of the fluid collection device allows the fluids collected in the cavity 154 to drain into the reservoir 172 when the device is positioned on the wearer. Locating the inlet of the additional conduit 108 at or near a location expected to be the gravimetrically low point of the cavity 154 when worn by a user enables the additional conduit 108 to receive more of the fluid(s) than if inlet was located elsewhere and reduce the likelihood of pooling (e.g., pooling of the fluid(s) may cause microbe growth and foul odors). For instance, the fluid(s) in the porous material 165 may flow in any direction due to capillary forces. However, the fluid(s) may exhibit a preference to flow in the direction of gravity, especially when at least a portion of the porous material 165 is saturated with the fluid(s). Accordingly, one or more of the inlet or the reservoir 172 may be located in the first end region 175. While depicted in the first end region 175, the reservoir 172 may be located in any portion of the cavity 154 such as the second end region 177. In such examples, the additional conduit 108 may extend into the reservoir 172, such as through one or more of the porous material 165 or fluid impermeable barrier 152 in the second end region 177.

Other embodiments of fluid impermeable barriers, fluid permeable membranes, fluid permeable supports, cavities, conduits and their shapes and configurations are disclosed in U.S. patent application Ser. No. 15/612,325 filed on Jun. 2, 2017; U.S. patent application Ser. No. 15/260,103 filed on Sep. 8, 2016; and U.S. Pat. No. 10,226,376 filed on Jun. 1, 2017, the disclosure of each of which is incorporated herein, in its entirety, by this reference.

During use, the opening the fluid collection device 150 may be positioned over the urethra of the wearer. Urine may be collected in the fluid collection device 150 and removed from the wearer to the fluid storage container, such as via gravity or vacuum force. At least a portion of bodily waste (e.g., liquid or semi-liquid stool) may be collected in the bodily waste collection apparatus and removed to the at least one fluid storage container, such as via gravity or vacuum force.

Returning to FIG. 5, the fluid storage container 180 may include a bag (e.g., drainage bag), a rigid bottle or cup (e.g., collection jar), or any other enclosed container for storing fluids. The at least one fluid storage container 180 may be fluidly connected to the at least one vacuum source 190, such as via a portion of the conduit 140 or additional conduit 108, respectively. The at least one vacuum source 190 provides a vacuum for pulling fluids from one or more of the fluid collection device 150 or the bodily waste collection apparatus 100 into the at least one fluid storage container 180 via the conduit 140 and additional conduit 108. The fluid collected in the one or more of the fluid collection device 150 or the bodily waste collection apparatus 100 is moved through conduit(s) 140 or 108 into the at least one fluid storage container 180. By having a separate connection to the vacuum source 190 on the fluid storage container(s) 180, the fluids removed from the fluid collection device 150 or the bodily waste collection apparatus 100 may be prevented from entering the vacuum source 190.

The at least one vacuum source 190 may include one or more of a manual vacuum pump, an electric vacuum pump, a diaphragm pump, a centrifugal pump, a displacement pump, a magnetically driven pump, a peristaltic pump, or any pump configured to produce a vacuum. The at least one vacuum source 190 may include a wall mounted suction line, such as found in a hospital room. In examples, the at least one vacuum source 190 may be powered by one or more of a power cord (e.g., connected to a power socket), one or more batteries, or even manual power (e.g., a hand operated vacuum pump). The at least one vacuum source 190 may include one or more of a switch, a button, a plug, a remote, or any other actuator suitable to activate the at least one vacuum source 190. The at least one vacuum source 190 may be selectively operated by a user (e.g., medical personnel, the wearer, or a caretaker).

Figure 8:
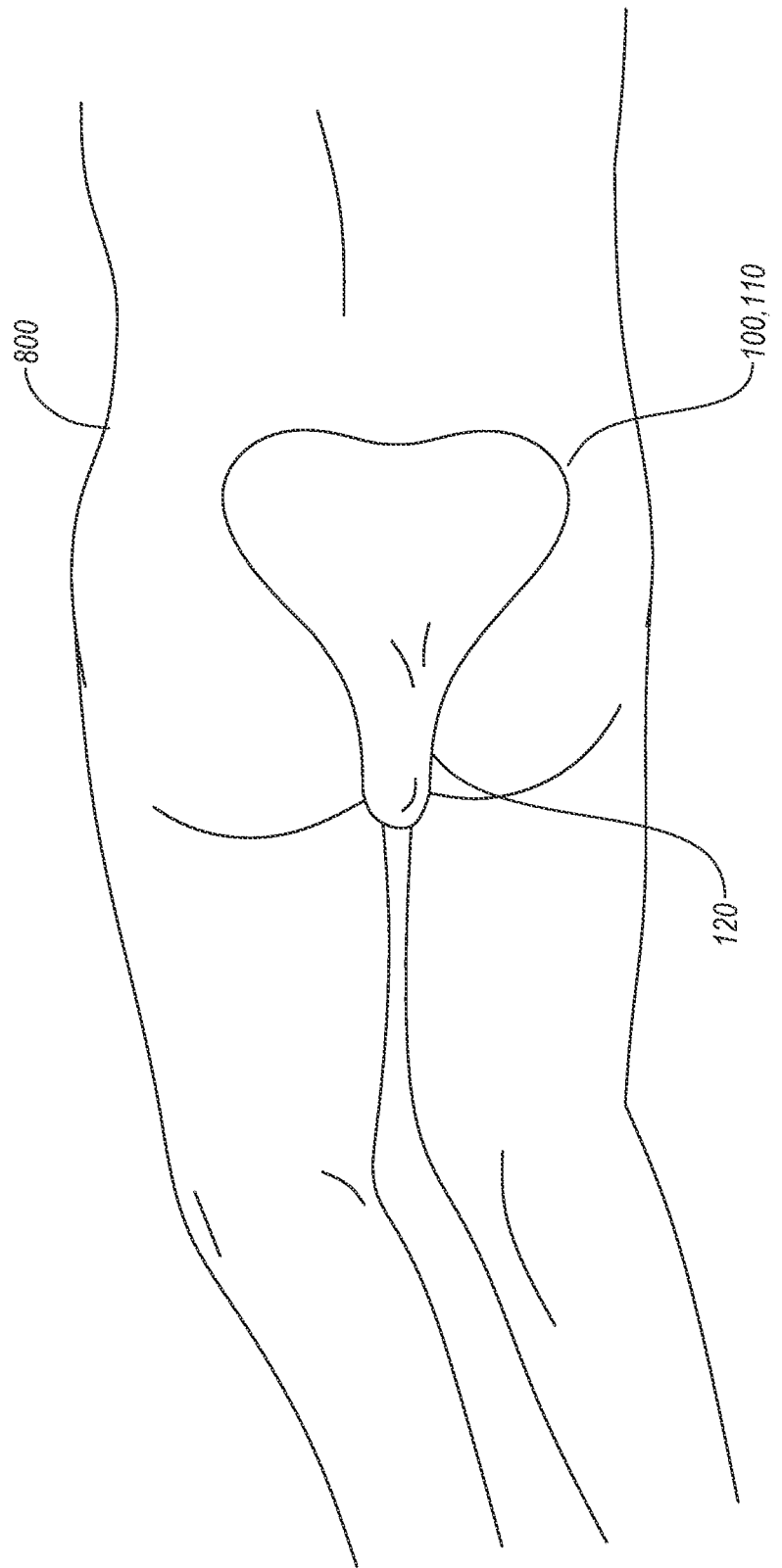
FIG. 8 is a schematic of a bodily waste collection apparatus positioned on a wearer during use, according to an embodiment.

FIG. 8 is a schematic of the bodily waste collection apparatus 100 positioned on a wearer 800 during use, according to an embodiment. During use, the sacral pad 110 of the bodily waste collection apparatus 100 is positioned over the sacrum of the wearer 800. The adhesive thereon maintains the position of the sacral pad 110 over the sacrum of the wearer 800, thereby protecting the sacrum from developing bed sores. The bodily waste collection device 120 is positioned over or at least partially within the intergluteal cleft of the wearer 800, with the opening thereof being disposed over (e.g., adjacent to) the anus of the wearer 800. Accordingly, the sacral pad 110 also at least partially maintains the position of the bodily waste collection device with respect to the anus of the wearer 800. The bodily waste collection device 120 may be at least partially deformed (e.g., squeezed, folded, etc.) to contour the anatomical features of the wearer 800 (e.g., bend along the sagittal plane, bend around the buttocks, at least partially fit within the intergluteal cleft, or the like).

Figure 9:
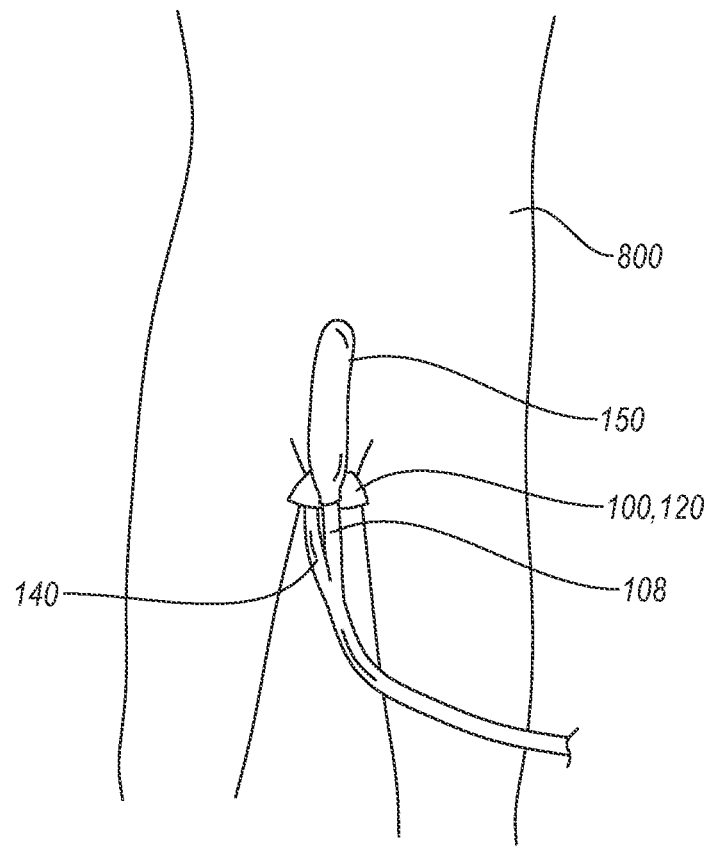
FIG. 9 is a schematic of a fluid collection device positioned on a wearer during use, according to an embodiment.

FIG. 9 is a schematic of the fluid collection device 150 positioned on a wearer 800 during use, according to an embodiment. When present, the fluid collection device 150 may be positioned over the urethra of the wearer 800. For example, the fluid collection device 150 may be positioned in the pelvic region of the wearer 800 such that the opening is disposed over (e.g., adjacent to) and facing the urethra of the wearer 800. As shown, the additional conduit 108 may be disposed in a downward position on a supine or laying wearer, thereby allowing fluid collected in the fluid collection device 150 to collect in the reservoir in the first end region thereof and to be removed from the reservoir via the inlet of the additional conduit 108 in the first end region. As shown, the bodily waste collection device of the bodily waste collection apparatus 100 is disposed near the anus of the wearer 800. Accordingly, the system 200, apparatus 100, and collection devices therein may collect bodily waste and fluids (e.g., liquid or semi-liquid stool, urine, etc.) from the wearer 800 to keep the wearer 800 dry and clean.

Figure 10:
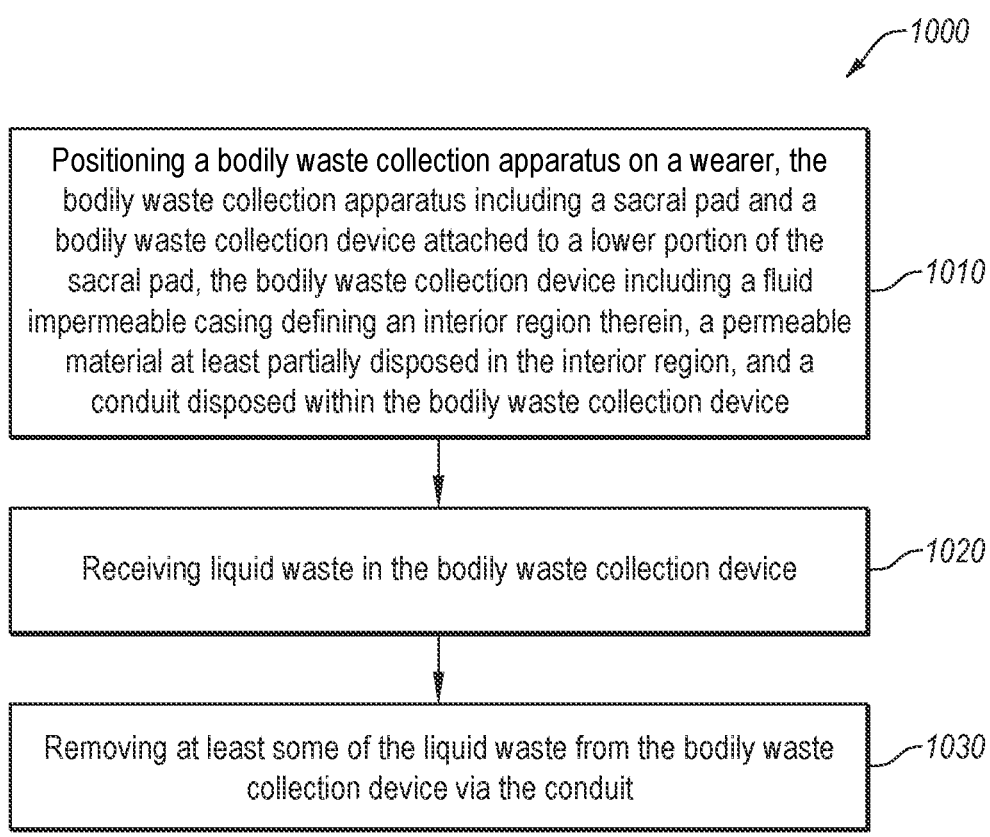
FIG. 10 is a flow diagram of a method for collecting bodily waste, according to an embodiment.

FIG. 10 is a flow diagram of a method 1000 for collecting bodily waste, according to an embodiment. The method 1000 includes block 1010, which recites "positioning a bodily waste collection apparatus on a wearer, the bodily waste collection apparatus including a sacral pad and a bodily waste collection device attached to a lower portion of the sacral pad, the bodily waste collection device including a fluid impermeable casing defining an interior region therein, a permeable material at least partially disposed in the interior region, and a conduit disposed within the bodily waste collection device." Block 1010 may be followed by block 1020, which recites "receiving liquid waste in the bodily waste collection device." Block 1020 may be followed by block 1030, which recites "removing at least some of the liquid waste from the bodily waste collection device via the conduit." Blocks 1010, 1020, 1030 of the method 1000 are for illustrative purposes. For example, the blocks may be modified, supplemented, split, or combined. In an example, one or more of the blocks 1010, 1020, 1030 of the method 1000 may be omitted from the method 1000. Any of the blocks 1010, 1020, or 1030 may include using any of the bodily waste collection systems, apparatuses, or collection devices disclosed herein.

Block 1010 recites "positioning a bodily waste collection apparatus on a wearer, the bodily waste collection apparatus including a sacral pad and a bodily waste collection device attached to a lower portion of the sacral pad, the bodily waste collection device including a fluid impermeable casing defining an interior region therein, a permeable material at least partially disposed in the interior region, and a conduit disposed within the bodily waste collection device." The bodily waste collection apparatus may include any of the bodily waste collection apparatuses disclosed herein. Positioning a bodily waste collection apparatus on a wearer may include positioning and attaching the sacral pad to over a sacrum of the wearer. The sacral pad may be attached by the adhesive thereon, such as by placing the adhesive in contact with the wearer.

Positioning a bodily waste collection apparatus on a wearer may include disposing the bodily waste collection device under, over, adjacent to, or on the anus of the wearer. Positioning a bodily waste collection apparatus on a wearer may include disposing the bodily waste collection device at least partially within the intergluteal cleft of the wearer. In such examples, the bodily waste collection device may be manipulated for positioning, such as by compressing, bending, folding, or otherwise forming the bodily waste collection device to at least partially conform to anatomical features of the wearer. The bodily waste collection device may be positioned under, over, adjacent to, or on the anus of the wearer prior to attaching the sacral pad to the wearer. Accordingly, the sacral pad may be used to at least partially maintain the position of the bodily waste collection device in a selected position during use.

Block 1020 recites "receiving liquid waste in the bodily waste collection device." Receiving liquid waste in the bodily waste collection device may include receiving at least partially liquid waste (e.g., liquid or semi-liquid stool) from the anus of the wearer. Receiving liquid waste in the bodily waste collection device may include receiving at least partially liquid stool in the bodily waste collection device. For example, receiving liquid waste in the bodily waste collection device may include receiving at least partially liquid waste (e.g., at least partially liquid stool) on the permeable material of the bodily waste collection device.

In some examples, receiving liquid waste in the bodily waste collection device may include receiving urine in the bodily waste collection device.

Block 1030 recites, "removing at least some of the liquid waste from the bodily waste collection device via the conduit." Removing at least some of the liquid waste from the bodily waste collection device via the conduit may include removing at least some of the liquid waste via gravity or vacuum force. For example, removing at least some of the liquid waste from the bodily waste collection device via the conduit may include applying a vacuum within the bodily waste collection device with the vacuum source.

The method 1000 may include positioning a fluid collection device on a wearer. The fluid collection device may include any of the fluid collection devices disclosed herein. For example, the fluid collection device may include a fluid impermeable barrier defining a cavity therein and an opening therethrough, a porous material disposed in the cavity, and an additional conduit disposed in the cavity. Positioning a fluid collection device on a wearer may include positioning the opening over (e.g., adjacent to) the urethra of the wearer.

The method 1000 may include receiving urine in the fluid collection device, such as from the urethra of the wearer. The method 1000 may include removing at least some of the urine from the fluid collection device, such as via one or more of gravity or vacuum force. For example, removing at least some of the urine from the fluid collection device may include applying a vacuum within the fluid collection device with the vacuum source via the (additional) conduit.

The sacral pad of the apparatuses, devices, systems, and methods disclosed herein both protects the sacrum of the wearer and securely positions the bodily waste collection device in a position for use on the wearer. The apparatuses, devices, systems, and methods disclosed herein allow wearers and health care providers to collect liquid or semi-liquid stool as well as urine from the wearer as soon as it is expelled to prevent the wearer's skin, clothing, and bedding from being soiled. Accordingly, the apparatuses, devices, systems, and methods disclosed herein prevent or limit supine patients from developing ulcers (e.g., bedsores) on their sacrum, keep the wearer's skin dry, maintain position of the bodily waste collection device with respect to the wearer's anus, and limit the amount of time necessary to care for the hygiene of supine or bedridden individuals. Additionally, the apparatuses, devices, systems, and methods disclosed herein prevent urinary tract infections by removing fecal material from the region around the wearer's urethra.

While various aspects and embodiments have been disclosed herein, other aspects and embodiments are contemplated. The various aspects and embodiment disclosed herein are for purposes of illustration and are not intended to be limiting. Features from any of the disclosed embodiments may be used in combination with one another, without limitation.

What is claimed is:

1. A bodily waste collection apparatus, comprising:
   a sacral pad including an adhesive disposed on a wearer-facing side thereof; and
   a bodily waste collection device attached to a lower portion of the sacral pad and positioned to receive bodily waste from the anus of a wearer, the bodily waste collection device including:
   a fluid impermeable casing defining an interior region therein and defining an opening through which the interior region communicates with an external environment;
   a permeable material at least partially disposed in the interior region and extending across at least a portion of the opening; and
   a conduit disposed within the bodily waste collection device.

2. The bodily waste collection apparatus of claim 1 wherein the sacral pad is sized and shaped to be attached to a wearer over a sacrum of the wearer and the bodily waste collection device is sized and shaped to be disposed over an anus of the wearer when the sacral pad is attached to the wearer over the sacrum.

3. The bodily waste collection apparatus of claim 1 wherein the bodily waste collection device is sized and shaped to at least partially fit within an intergluteal cleft of a wearer when the sacral pad is attached to a wearer over a sacrum of the wearer.

4. The bodily waste collection apparatus of claim 1 wherein the sacral pad includes:
padding material in a central region of the sacral pad; and
the adhesive is disposed around the padding material.

5. The bodily waste collection apparatus of claim 4 wherein sacral pad includes a backing material where the padding material and adhesive are disposed on a wearer-facing side of the backing material.

6. The bodily waste collection apparatus of claim 1 wherein the permeable material includes a fluid permeable sheath and a fluid permeable base disposed at least partially under the fluid permeable sheath.

7. The bodily waste collection apparatus of claim 1 wherein the conduit extends into the permeable material.

8. The bodily waste collection apparatus of claim 1, further comprising at least one fluid collection device, the at least one fluid collection device including:
a fluid impermeable barrier defining a cavity therein;
a porous material disposed in the cavity; and
an additional conduit disposed in the cavity.

9. The bodily waste collection apparatus of claim 8 wherein the conduit and the additional conduit are coupled to each other.

10. A bodily waste collection system, comprising:
at least one fluid storage container configured to hold a fluid;
a bodily waste collection apparatus including:
    a sacral pad including an adhesive disposed on a wearer-facing side thereof; and
    a bodily waste collection device attached to a lower portion of the sacral pad and positioned to receive bodily waste from the anus of a wearer, the bodily waste collection device including:
        a fluid impermeable casing defining an interior region therein and defining an opening through which the interior region communicates with an external environment;
        a permeable material at least partially disposed in the interior region and extending across at least a portion of the opening; and
        a conduit disposed within the bodily waste collection device; and
at least one vacuum source fluidly connected to the at least one fluid storage container via the conduit, the at least one vacuum source configured to draw fluid into the at least one fluid storage container from the bodily waste collection device via the conduit.

11. The bodily waste collection system of claim 10, further comprising a fluid collection device fluidly coupled to the at least one fluid storage container via an additional conduit, wherein the at least one fluid collection device includes:
a fluid impermeable barrier defining a cavity therein;
a porous material disposed in the cavity; and
the additional conduit disposed in the cavity.

12. The bodily waste collection system of claim 11 wherein:
the at least one fluid storage container includes a first fluid storage container and a second storage container;
the first fluid storage container is fluid connected to the bodily waste collection device;
the second fluid storage container is fluidly connected to the fluid collection device; and
the first fluid storage container and the second fluid storage container are fluidly connected to the at least one vacuum source.

13. The bodily waste collection system of claim 12 wherein the at least one vacuum source includes a first vacuum source fluidly connected to the first fluid storage container and a second vacuum source fluidly connected to the second fluid storage container.

14. The bodily waste collection system of claim 10 wherein the sacral pad is sized and shaped to be attached to a wearer over a sacrum of the wearer and the bodily waste collection device is sized and shaped to be disposed over an anus of the wearer when the sacral pad is attached to the wearer over the sacrum.

15. The bodily waste collection system of claim 10 wherein the sacral pad includes:
padding material in a central region of the sacral pad; and
the adhesive is disposed around the padding material.

16. A method for collecting bodily waste, the method comprising:
positioning a bodily waste collection apparatus on a wearer, the bodily waste collection apparatus including:
    a sacral pad including an adhesive disposed on a wearer-facing side thereof; and
    a bodily waste collection device attached to a lower portion of the sacral pad and positioned to receive bodily waste from the anus of a wearer, the bodily waste collection device including:
        a fluid impermeable casing defining an interior region therein and defining an opening through which the interior region communicates with an external environment;
        a permeable material at least partially disposed in the interior region and extending across at least a portion of the opening; and
        a conduit disposed within the bodily waste collection device;
receiving liquid waste in the bodily waste collection device; and
removing at least some of the liquid waste from the bodily waste collection device via the conduit.

17. The method of claim 16 wherein positioning the bodily waste collection apparatus on a wearer includes positioning and attaching the sacral pad to over a sacrum of the wearer.

18. The method of claim 16 wherein positioning the bodily waste collection apparatus on a wearer includes disposing the bodily waste collection device under an anus of the wearer.

19. The method of claim 16 wherein positioning the bodily waste collection apparatus on a wearer includes disposing the bodily waste collection device at least partially within an intergluteal cleft of the wearer.

20. The method of claim 16 wherein receiving liquid waste in the bodily waste collection device includes receiving at least partially liquid stool in the bodily waste collection device.

21. The method of claim 16 wherein removing at least some of the liquid waste from the bodily waste collection device via the conduit includes removing at least some of the liquid waste via gravity or vacuum force.

22. The method of claim 16, further comprising positioning a fluid collection device on the wearer, the fluid collection device including:
- a fluid impermeable barrier defining a cavity therein and an opening therethrough;
- a porous material disposed in the cavity; and
- an additional conduit disposed in the cavity.

23. The method of claim 22 wherein positioning a fluid collection device on the wearer includes positioning the opening over a urethra of the wearer.

24. The method of claim 23, further comprising receiving urine in the fluid collection device.

25. The method of claim 24, further comprising removing at least some of the urine from the fluid collection device.

\* \* \* \* \*